(12) United States Patent
Xian

(10) Patent No.: US 11,236,083 B2
(45) Date of Patent: Feb. 1, 2022

(54) COMPOUNDS AND PHARMACEUTICAL COMPOSITIONS FOR MODULATING SGK ACTIVITY, AND METHODS THEREOF

(71) Applicant: NEW ERA PHARMA, INC., Southborough, MA (US)

(72) Inventor: Jun Xian, Sharon, MA (US)

(73) Assignee: ORIMOS THERAPEUTICS CO., LTD., Nanjing (CN)

(*) Notice: Subject to any disclaimer, the term of this patent is extended or adjusted under 35 U.S.C. 154(b) by 124 days.

(21) Appl. No.: 16/343,826

(22) PCT Filed: Nov. 24, 2017

(86) PCT No.: PCT/US2017/063179
§ 371 (c)(1),
(2) Date: Apr. 22, 2019

(87) PCT Pub. No.: WO2018/106459
PCT Pub. Date: Jun. 14, 2018

(65) Prior Publication Data
US 2021/0032239 A1     Feb. 4, 2021

Related U.S. Application Data

(60) Provisional application No. 62/431,203, filed on Dec. 7, 2016.

(51) Int. Cl.
| | | |
|---|---|---|
| C07D 401/04 | (2006.01) |
| C07D 403/04 | (2006.01) |
| C07D 407/14 | (2006.01) |
| C07D 471/04 | (2006.01) |
| C07D 231/56 | (2006.01) |
| C07D 401/10 | (2006.01) |
| C07D 403/10 | (2006.01) |
| C07D 405/12 | (2006.01) |
| C07D 413/12 | (2006.01) |
| C07D 487/16 | (2006.01) |
| C07D 491/06 | (2006.01) |

(52) U.S. Cl.
CPC ......... *C07D 471/04* (2013.01); *C07D 231/56* (2013.01); *C07D 401/10* (2013.01); *C07D 403/10* (2013.01); *C07D 405/12* (2013.01); *C07D 413/12* (2013.01); *C07D 487/16* (2013.01); *C07D 491/06* (2013.01)

(58) Field of Classification Search
CPC ... C07D 401/04; C07D 403/04; C07D 407/14
See application file for complete search history.

(56) References Cited

U.S. PATENT DOCUMENTS
9,174,993 B2 * 11/2015 Nazare ................ A61P 19/02
2008/0182844 A1    7/2008 Bjergarde et al.

FOREIGN PATENT DOCUMENTS
| | | |
|---|---|---|
| WO | 2013/041119 A1 | 3/2013 |
| WO | 2014/140065 A1 | 9/2014 |

OTHER PUBLICATIONS
Banker et al. "Modern Pharmaceutics", 3rd Ed. p. 596 (1996). (Year: 1996).*
"Burger's Medicinal Chemistry", edited by Manfred E.Wolf, 5th Ed. Part 1, pp. 975-977 (1995). (Year: 1995).*
Evans in "Principles of Radiopharmacology", Colombett, L.G. editor, CRC Press, pp. 11-13 and 24 (1979).*
PCT/US17/63179, Int'l Search Report and Written Opinion of the ISA, Mar. 29, 2018.
Halland et al. ACS Medicinal Chemistry Letters, 6(1), pp. 73-78, Jan. 8, 2015.

\* cited by examiner

*Primary Examiner* — Emily A Bernhardt
(74) *Attorney, Agent, or Firm* — TomanageIP; Anna Tsang

(57) ABSTRACT

The present invention provides compounds of Formula (I) which can be used as SGK inhibitors; pharmaceutical compositions comprising the compounds of the invention; as well as uses and methods for treating a disease mediated by SGK by administering the compounds of the invention.

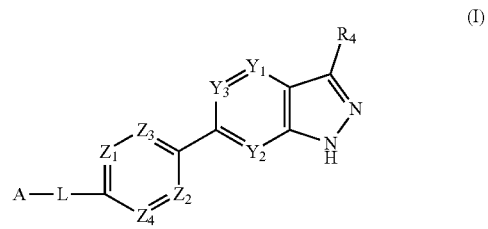

6 Claims, 8 Drawing Sheets

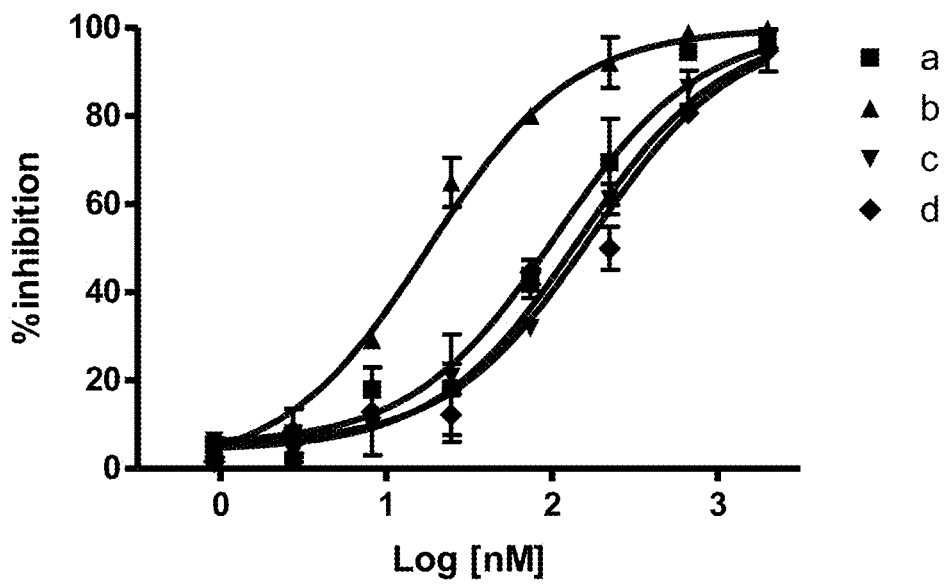
FIG. 1
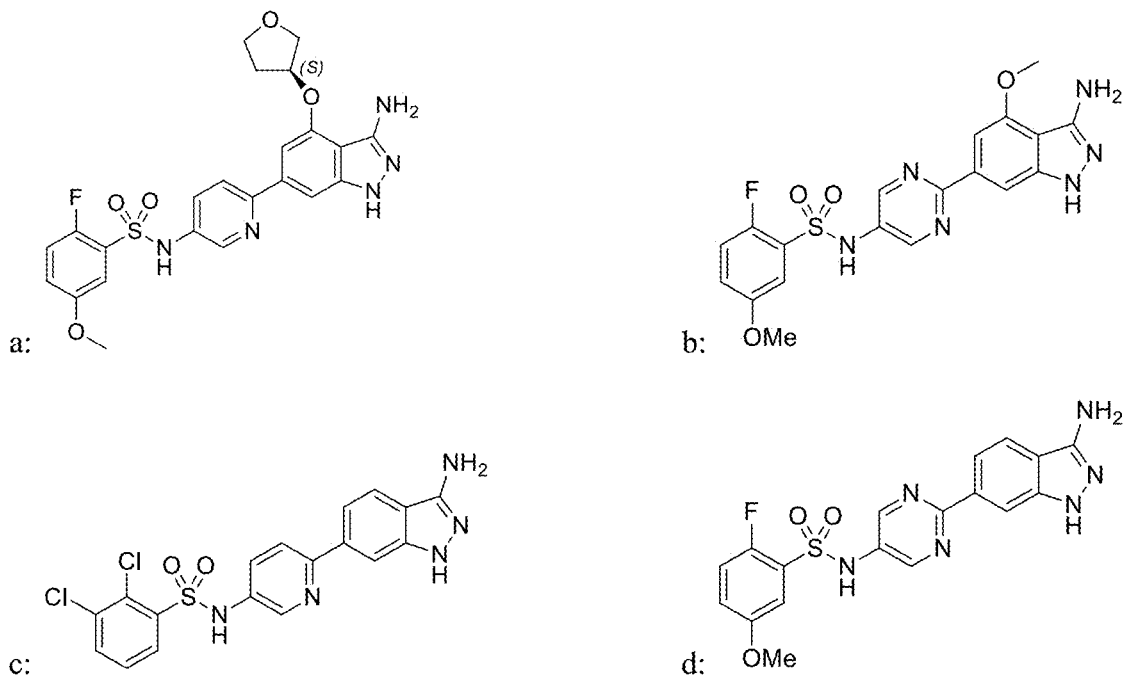

Concentration-Time Curve of Compound N in Male ICR Mice Following Intravenous and Oral Administration

COMPOUNDS AND PHARMACEUTICAL COMPOSITIONS FOR MODULATING SGK ACTIVITY, AND METHODS THEREOF

PRIORITY CLAIMS AND RELATED APPLICATIONS

This application is the US national phase of and claims priority to PCT/US17/63179, filed Nov. 24, 2017, which claims the benefit of priority to U.S. Provisional Application Ser. No. 62/431,203, filed on Dec. 7, 2016, the entire content of each of which is incorporated herein by reference in its entirety.

TECHNICAL FIELDS OF THE INVENTION

The invention generally relates to therapeutics and treatment methods for certain diseases and conditions. More particularly, the invention provides novel chemical compounds and pharmaceutical compositions thereof effective in modulating the activity of serum and glucocorticoid-regulated kinase (SGK) and methods of preparation and use thereof. The compounds and pharmaceutical compositions of the invention are suitable for use in treating, preventing, or reducing one or more of autoimmune diseases, cancer, cardiovascular diseases, inflammatory diseases and diabetes, or a related disease or disorder thereof.

BACKGROUND OF THE INVENTION

SGK (a.k.a. serine/threonine-protein kinase) is a subfamily of serine/threonine kinases that is under acute transcriptional control by several stimuli, including serum and glucocorticoids. In most vertebrates, including humans, there are three isoforms encoded by the genes SGK1, SGK2, and SGK3, among which the SGK1 gene has been most intensively studied. SGK1 is activated by insulin and growth factors via phosphatidylinositide-3-kinase, phosphoinositide-dependent kinase PDK1 and mammalian target of rapamycin mTORC2 and contributes to the regulation of transport, hormone release, neuroexcitability, inflammation, cell proliferation and apoptosis. Studies have shown that SGK1 expression is regulated during both discrete developmental stages and pathological conditions such as hypertension, diabetic neuropathy, ischemia, trauma, and neuro-degenerative diseases. (Lang et al. 2010 *The Journal of Physiology* 588: 3349-3354; Lang et al. 2013 *FASEB Journal.* 27 (1): 3-12; Schoenebeck et al. 2005 *Molecular and Cellular Neurosciences* 30 (2): 249-264.)

SGK1 has been implicated in mediating insulin, IGF1 (Insulin like Growth Factor 1), glucocorticoid, and IL2 (Interleukin2)-dependent survival signals in normal and cancer cells. The anti-apoptotic function of SGK1 implies its possible involvement in human carcinogenesis. SGK1 increased expression has been found in human tumors, for example, prostate cancer and non-small cell lung cancer of the squamous subtype, where SGK1 mRNA level correlates with several clinical prognostic indicators. The active SGK1 kinase regulates cell survival, proliferation and differentiation through Mdm2 (Mouse Double Minute 2), which directs p53 to ubiquitylation and proteosomal degradation. (Leong et al. *J Biol Chem* 2003 278:5871-5882; Mikosz et al. 2001 *J Biol Chem* 276:16649-16654; Wu et al. 2004 *Cancer Res* 64:1757-1764; Chung et al. 2002 *Mol Cells* 14:382-387; Amato et al. 2007 *J Mol Med* 85:707-721; Sherk et al. 2008 *Cancer Res* 68:7475-7483; Abbruzzese et al. 2012 *J Exp Clin Cancer Res* 31:4; Nasir et al. 2009 *IUBMB Life* 61:768-776; Amato et al. 2009 *J Mol Med* 87:1221-1239; Amato et al. 2013 *Oncogene* 32:4572-4578; D'Antona et al. 2015 *Cell Physiol Biochem* 35:2006-2018.)

Studies have shown that SGK2 become important for cell proliferation/viability as primary epithelial cells lose p53 tumor suppressor activity and remain important during tumor development. As the loss of p53 tumor suppressor activity is the most common hallmark of human tumorigenesis, the synthetic lethality with SGK2 loss suggests that this protein may be evaluated as a potential chemotherapeutic target. (2010 *Proc Natl Acad Sci USA* 107(28): 12463-12468.)

Additionally, studies have used transcriptional profiling of developing Th17 cells to construct a model of their signaling network and nominate major nodes that regulate Th17 development. SGK1 was identified as an essential node downstream of IL-23 signaling. SGK1 is critical for regulating IL-23R expression and stabilizing the Th17 cell phenotype by deactivation of Foxo1, a direct repressor of IL-23R expression. SGK1 has been shown to govern Na+ transport and salt (NaCl) homeostasis in other cells. Data from various studies have demonstrated that SGK1 plays a critical role in the induction of pathogenic Th17 cells and provides a molecular insight into a mechanism by which environmental factors such as a high salt diet triggers Th17 development and promotes tissue inflammation. (Wu et al. 2013 *Nature* 496(7446): 513-517.)

There is an urgent and growing need for improved therapeutics and treatment methods for autoimmune diseases, cancer, cardiovascular diseases, inflammatory diseases and diabetes, or a related disease or disorder thereof.

BRIEF DESCRIPTION OF THE DRAWINGS

In the following figures, the present invention is described by way of examples, wherein FIG. 1 schematically shows the data of Sgk1 $IC_{50}$ determination of compound a, b, c, FIG. 2 schematically shows a concentration-time curve of compound N in male ICR mice following intravenous and oral administration.

SUMMARY OF THE INVENTION

Figure 2:
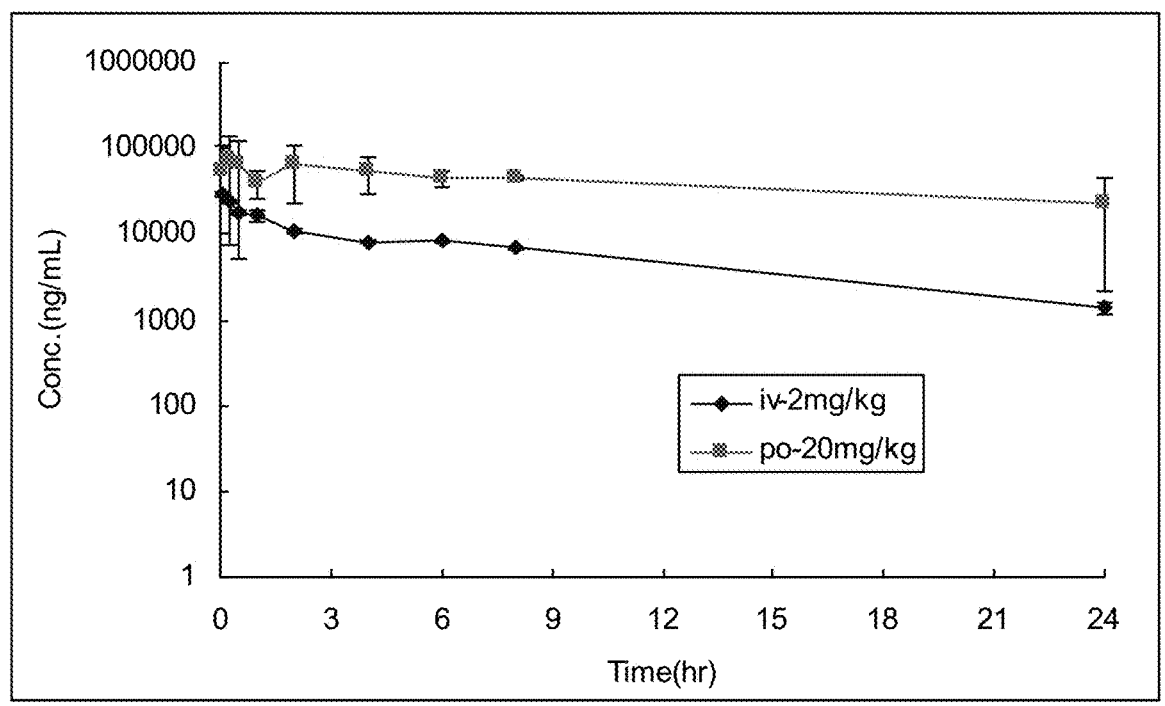

The invention provides novel, orally available, selective and potent compounds and pharmaceutical compositions thereof that effectively modulate the activity of SGK, in particular SGK1 and SGK2. The compounds and pharmaceutical compositions of the invention are suitable for use in treating, preventing, or reducing one or more of autoimmune diseases, cancer, cardiovascular diseases, inflammatory diseases and diabetes, or a related disease or disorder thereof.

In one aspect, the invention generally relates to a compound having the structural formula of (I):

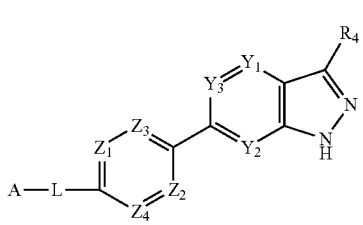

(I)

wherein,

A is an aryl group selected from the group consisting of unsubstituted 5- or 6-membered aryl groups and substituted 5- or 6-membered aryl groups;

L is a linking group comprising

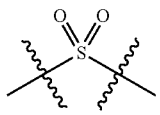 [SMILES: *S(*)(=O)=O]

$Y_1$ is $CR_1$ or N, wherein $R_1$ is a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group;

$Y_2$ is $CR_2$ or N, wherein $R_2$ is H, or a $C_1$-$C_6$ alkyl group;

$Y_3$ is $CR_3$ or N, wherein $R_3$ is H, or a $C_1$-$C_6$ alkyl group;

each of $Z_1$, $Z_2$, $Z_3$ and $Z_4$ is independently selected from the group consisting of CR and N, wherein R is H or a $C_1$-$C_6$ alkyl group; and $R_4$ is H, a $C_1$-$C_6$ alkyl group, —N(R')R", —N(R')—C(O)R", —N(R')—C(O)—NH—R", R'—O—R", wherein each of R' and R" is independently selected from the group consisting of H and a $C_1$-$C_6$ alkyl group, wherein $R_4$ and $Y_1$ optionally may join together to form a 5- to 8-membered ring, or a pharmaceutically acceptable form thereof.

In another aspect, the invention generally relates to a pharmaceutical composition comprising an amount of a compound having the structural formula of (I):

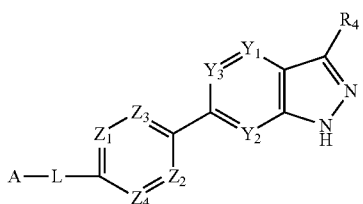

(I)

wherein,

A is an aryl group selected from the group consisting of unsubstituted 5- or 6-membered aryl groups and substituted 5- or 6-membered aryl groups;

L is a linking group comprising

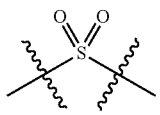 [SMILES: *S(*)(=O)=O]

$Y_1$ is $CR_1$ or N, wherein $R_1$ is a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group;

$Y_2$ is $CR_2$ or N, wherein $R_2$ is H, or a $C_1$-$C_6$ alkyl group;

$Y_3$ is $CR_3$ or N, wherein $R_3$ is H, or a $C_1$-$C_6$ alkyl group;

each of $Z_1$, $Z_2$, $Z_3$ and $Z_4$ is independently selected from the group consisting of CR and N, wherein R is H or a $C_1$-$C_6$ alkyl group; and $R_4$ is H, a $C_1$-$C_6$ alkyl group, —N(R')R", —N(R')—C(O)R", —N(R')—C(O)—NH—R", R'—O—R", wherein each of R' and R" is independently selected from the group consisting of H and a $C_1$-$C_6$ alkyl group, wherein $R_4$ and $Y_1$ optionally may join together to form a 5- to 8-membered ring, or a pharmaceutically acceptable form thereof, effective to treat, prevent, or reduce one or more diseases or disorders, in a mammal, including a human, and a pharmaceutically acceptable excipient, carrier, or diluent.

In yet another aspect, the invention relates to a unit dosage form comprising a pharmaceutical composition disclosed herein.

In yet another aspect, the invention relates to a method for treating, reducing, or preventing a disease or disorder, comprising administering to a subject in need thereof a pharmaceutical composition comprising a compound having the structural formula of (I):

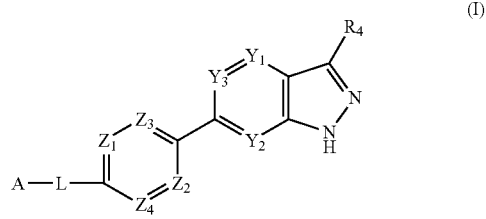

(I)

wherein,

A is an aryl group selected from the group consisting of unsubstituted 5- or 6-membered aryl groups and substituted 5- or 6-membered aryl groups;

L is a linking group comprising

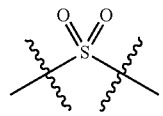

$Y_1$ is $CR_1$ or N, wherein $R_1$ is a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group;

$Y_2$ is $CR_2$ or N, wherein $R_2$ is H, or a $C_1$-$C_6$ alkyl group;

$Y_3$ is $CR_3$ or N, wherein $R_3$ is H, or a $C_1$-$C_6$ alkyl group;

each of $Z_1$, $Z_2$, $Z_3$ and $Z_4$ is independently selected from the group consisting of CR and N, wherein R is H or a $C_1$-$C_6$ alkyl group; and $R_4$ is H, a $C_1$-$C_6$ alkyl group, —N(R')R", —N(R')—C(O)R", —N(R')—C(O)—NH—R", R'—O—R", wherein each of R' and R" is independently selected from the group consisting of H and a $C_1$-$C_6$ alkyl group, wherein $R_4$ and $Y_1$ optionally may join together to form a 5- to 8-membered ring, or a pharmaceutically acceptable form thereof, effective to treat, prevent, or reduce one or more of autoimmune disease or disorder, cancer, a cardiovascular disease or disorder, inflammatory disease or disorder and diabetes, or a related disease or disorder thereof, in a mammal, including a human, and a pharmaceutically acceptable excipient, carrier, or diluent.

These and other features, aspects and advantages of the present invention will become better understood with reference to the following description, claims, and drawings, if any.

Definitions

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the terms "effective amount" or "therapeutically effective amount" refer to that amount of a compound or pharmaceutical composition described herein that is sufficient to effect the intended application including, but not limited to, disease treatment, as illustrated below.

In some embodiments, the amount is that effective for detectable killing or inhibition of the growth or spread of cancer cells; the size or number of tumors; or other measure of the level, stage, progression or severity of the cancer. In some embodiments, the amount is that effective for stop the progression or effect reduction of an autoimmune disease or disorder. In some embodiments, the amount is that effective for stop the progression or effect reduction of a cardiovascular disease or disorder. In some embodiments, the amount is that effective for stop the progression or effect reduction of inflammatory disease or disorder. In some embodiments, the amount is that effective for stop the progression or effect reduction of diabetes of a related disease or disorder.

The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "pharmaceutically acceptable ester" refers to esters that hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxy or carboxylic acid group of the parent compound.

As used herein, the term "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, esters, hydrates, solvates, isomers, prodrugs, and isotopically labeled derivatives of disclosed compounds. In one embodiment, a "pharmaceutically acceptable form" includes, but is not limited to, pharmaceutically acceptable salts, esters, isomers, prodrugs and isotopically labeled derivatives of disclosed compounds. In some embodiments, a "pharmaceutically acceptable form" includes, but is not limited to, pharmaceutically acceptable salts, esters, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group which encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl), which has at least one ring having a conjugated pi electron system that is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—$OR^a$, —$SR^a$, —OC(O)—$R^a$, —N($R^a$)$_2$, —C(O)$R_a$, —C(O)$OR^a$, —OC(O)N($R^a$)$_2$, —C(O)N($R^a$)$_2$, —N($R^a$) C(O)$OR^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R^a$, —C(O)$OR^a$, —OC(O)N($R^a$)$_2$, —C(O)N($R^a$)$_2$, —N($R^a$)C (O)$OR^a$, —N($R^a$)C(O)$R^a$, —N($R^a$)C(O)N($R^a$)$_2$, —N($R^a$)C (N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halide", "halo", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoroethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl that refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5]thieno [2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

DETAILED DESCRIPTION OF THE INVENTION

The invention is based on the unexpected discovery of novel, orally available, selective and potent compounds and pharmaceutical compositions thereof that effectively modulate the activity of SGK, in particular SGK1 and SGK2. The compounds and pharmaceutical compositions of the invention are suitable for use in treating, preventing, or reducing one or more of autoimmune diseases, cancer, cardiovascular diseases, inflammatory diseases and diabetes, or a related disease or disorder thereof.

For example, studies have shown that SGK1 selectively and reciprocally regulates helper T cell differentiation downstream of mTORC2. Inhibition of SGK1 impacts autoimmune diseases mediated by Th2 immune responses. In regard to cancer and tumors, inhibition SGK1 influences cell proliferation and apoptosis, thus can be therapeutically used to treat cancers and tumors.

In one aspect, the invention generally relates to a compound having the structural formula of (I):

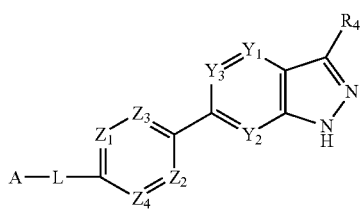

(I)

wherein,

A is an aryl group selected from the group consisting of unsubstituted 5- or 6-membered aryl groups and substituted 5- or 6-membered aryl groups;

L is a linking group comprising

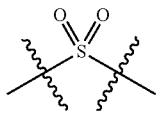 [SMILES: *S(*)(=O)=O]

$Y_1$ is $CR_1$ or N, wherein $R_1$ is a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group;

$Y_2$ is $CR_2$ or N, wherein $R_2$ is H, or a $C_1$-$C_6$ alkyl group;

$Y_3$ is $CR_3$ or N, wherein $R_3$ is H, or a $C_1$-$C_6$ alkyl group;

each of $Z_1$, $Z_2$, $Z_3$ and $Z_4$ is independently selected from the group consisting of CR and N, wherein R is H or a $C_1$-$C_6$ alkyl group; and $R_4$ is H, a $C_1$-$C_6$ alkyl group, —N(R')R", —N(R')—C(O)R", —N(R')—C(O)—NH—R", R'—O—R", wherein each of R' and R" is independently selected from the group consisting of H and a $C_1$-$C_6$ alkyl group, wherein $R_4$ and $Y_1$ optionally may join together to form a 5- to 8-membered ring, or a pharmaceutically acceptable form thereof.

L may be any suitable linking group. In certain preferred embodiments, L is a group that comprises

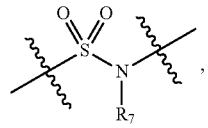

wherein $R_7$ is H or a $C_1$-$C_6$ alkyl group.

A may be any suitable unsubstituted or substituted 5- or 6-membered aryl group, including hetero-aryl groups. In certain preferred embodiments, A is selected from the group consisting of:

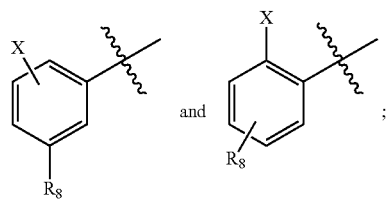

wherein X is a halogen atom and $R_8$ is $OR_7$, wherein $R_7$ is H or a $C_1$-$C_6$ alkyl group.

Embodiments of the invention include none of, one of, two of $Y_1$, $Y_2$ and $Y_3$ being N atoms. In certain embodiments, $Y_1$=$CR_1$, $Y_2$=$CR_2$, $Y_3$=$CR_3$. In certain embodiments, $Y_1$=$CR_1$, $Y_2$=N, $Y_3$=$CR_3$. In certain embodiments, $Y_1$=$CR_1$, $Y_2$=$CR_2$, $Y_3$=N. In certain embodiments, $Y_1$=N, $Y_2$=N, $Y_3$=$CR_3$. In certain embodiments, $Y_1$=N, $Y_2$=$CR_2$, $Y_3$=N. Here, each $R_1$ is independently selected from a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group; each $R_2$ is independently selected from the group consisting of H and a $C_1$-$C_6$ alkyl group; and each $R_3$ is independently selected from the group consisting of H and a $C_1$-$C_6$ alkyl group. In certain embodiments, each of $R_1$, $R_2$ and $R_3$ is H.

Each of $Z_1$, $Z_2$, $Z_3$ and $Z_4$ is independently selected from the group consisting of CR and N, wherein R is H or a $C_1$-$C_6$ alkyl group. Embodiments of the invention include none of, one of, two of, or three of $Z_1$, $Z_2$, $Z_3$ and $Z_4$ being N atoms. In certain preferred embodiments, one of $Z_1$, $Z_2$, $Z_3$ and $Z_4$ is N. In certain preferred embodiments, one of $Z_1$ and $Z_3$ is N and one of $Z_2$ and $Z_4$ is N.

In certain preferred embodiments, $Z_3$ is —$CR_5$ and $Z_4$ is —$CR_6$, and the compound has the structural formula:

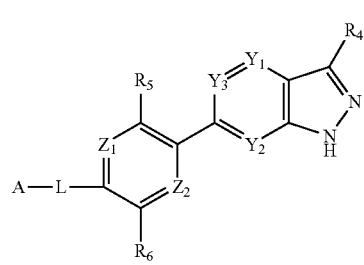

(II)

wherein $R_5$ is H or a $C_1$-$C_6$ alkyl group; and $R_6$ is H or a $C_1$-$C_6$ alkyl group.

In certain embodiments, each of $Z_1$ and $Z_2$ is N and each of $Z_3$ and $Z_4$ is not N. In certain preferred embodiments, $Z_1$=$Z_2$=CR. In certain embodiments, $Z_1$=$Z_2$=N. In certain embodiments, $Z_1$=N, $Z_2$=CR. In certain embodiments, $Z_1$=CR, $Z_2$=N. In certain embodiments, each R is H.

In certain embodiments, a compound of the invention has the structural formula:

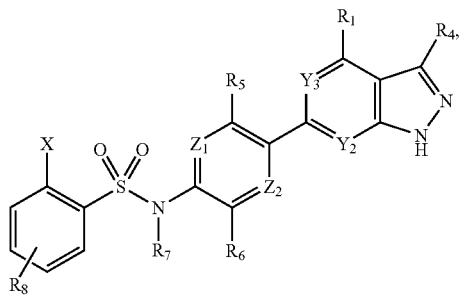

(III)

wherein X, $Y_2$, $Y_3$, $Z_1$, $Z_2$, $R_1$, $R_4$, $R_5$, $R_6$, $R_7$ and $R_8$ are as herein defined.

In certain embodiments, a compound of the invention has the structural formula:

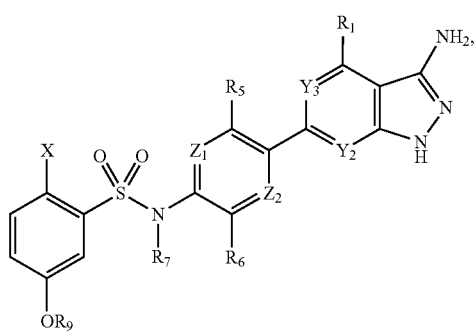

(IV)

wherein X, $Y_2$, $Y_3$, $Z_1$, $Z_2$, $R_1$, $R_5$, $R_6$, $R_7$ and $R_9$ are as herein defined.

In certain preferred embodiments of (III) or (IV), X is F or Cl, $R_5$=$R_6$=$R_7$=H, $R_4$ is $NH_2$, $R_8$ is $OR_9$, wherein $R_9$ is a hydrogen or a $C_1$-$C_6$ alkyl group.

In certain preferred embodiments of (III) or (IV), at least one of $Z_1$ and $Z_2$ is N.

In certain preferred embodiments of (III) or (IV), at least one of $Y_2$ and $Y_3$ is not N.

In certain embodiments, a compound of the invention has the structural formula:

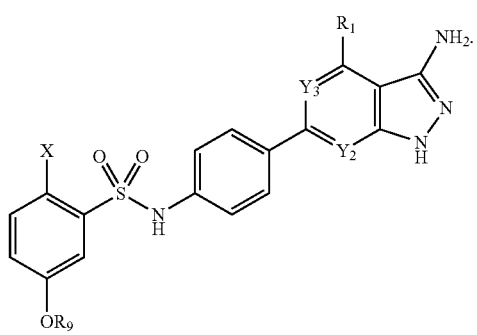

(V)

In certain embodiments of (V), X is F, $R_9$ is $CH_3$, $Y_2$ is CH, $Y_3$ is N, and $R_1$ is a $C_1$-$C_6$ alkyl group. In certain preferred embodiments, $R_1$ is $CH_3$.

In certain embodiments of (V), X is F, $R_9$ is $CH_3$, $Y_2$ is N, $Y_3$ is CH, and $R_1$ is a $C_1$-$C_6$ alkyl group. In certain preferred embodiments, $R_1$ is $CH_3$.

In certain embodiments of (V), X is F, $R_9$ is $CH_3$, $Y_2$ is CH, $Y_3$ is CH, and $R_1$ is a $C_1$-$C_6$ alkyl group. In certain preferred embodiments, $R_1$ is $CH_3$.

In certain embodiments of (I), $R_4$ and $Y_1$ optionally may join together to form a 5- to 8-membered ring Q, having the structural formula:

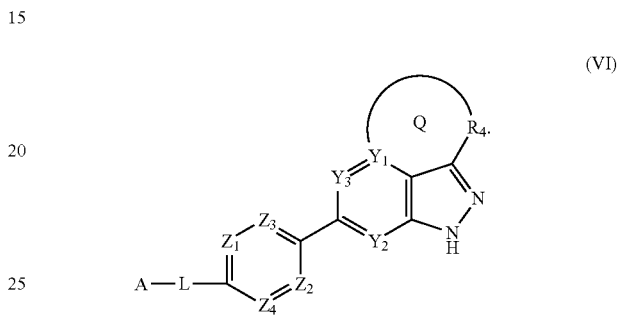

(VI)

Q may be any suitable a 6- or 7-membered cyclic moiety, including hetero-cyclic rings.

In certain embodiments of (VI), $Y_1$=$CR_1$, $Y_2$=$CR_2$, $Y_3$=$CR_3$. In certain embodiments, $Y_1$=CRI, $Y_2$=N, $Y_3$=$CR_3$. In certain embodiments, $Y_1$=$CR_1$, $Y_2$=$CR_2$, $Y_3$=N. In certain embodiments, $Y_1$=N, $Y_2$=N, $Y_3$=$CR_3$. In certain embodiments, $Y_1$=N, $Y_2$=$CR_2$, $Y_3$=N.

In certain embodiments of (VI), each of $Z_1$ and $Z_2$ is N and each of $Z_3$ and $Z_4$ is not N. In certain embodiments, $Z_3$=$Z_4$=CH. In certain preferred embodiments, $Z_1$=$Z_2$=CR. In certain embodiments, $Z_1$=$Z_2$=N. In certain embodiments, $Z_1$=N, $Z_2$=CR. In certain embodiments, $Z_1$=CR, $Z_2$=N. In certain embodiments, each R is H.

TABLE 1

Exemplary Compounds

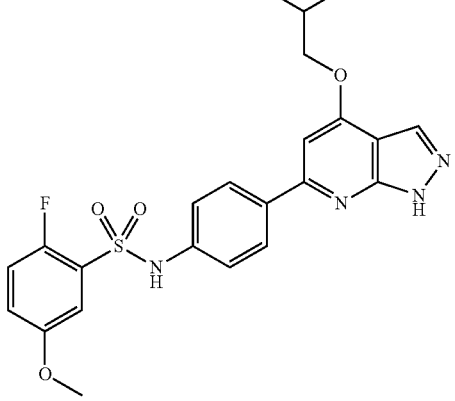

TABLE 1-continued
Exemplary Compounds
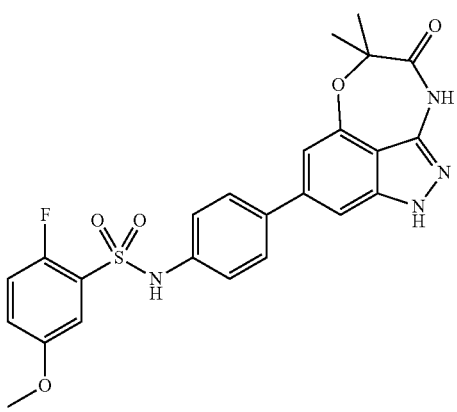 [SMILES: COc1ccc(F)c(S(=O)(=O)Nc2ccc(-c3cc4c5c(n[nH]c5c3)NC(=O)C(C)(C)O4)cc2)c1]
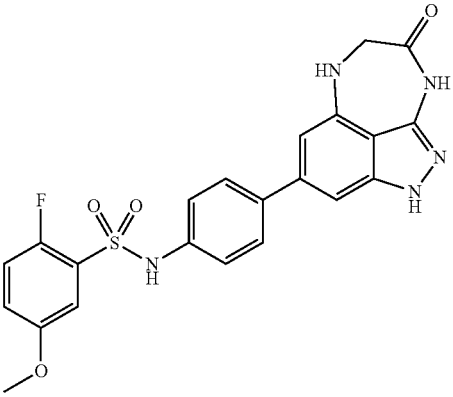
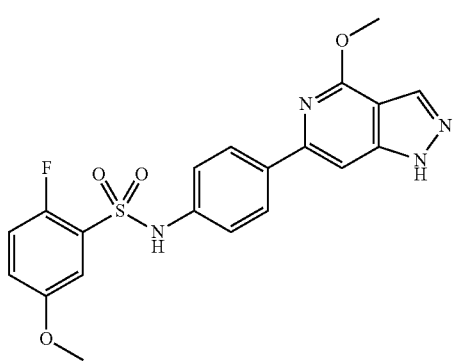 [SMILES: COc1ccc(F)c(S(=O)(=O)Nc2ccc(-c3cc4[nH]ncc4c(OC)n3)cc2)c1]
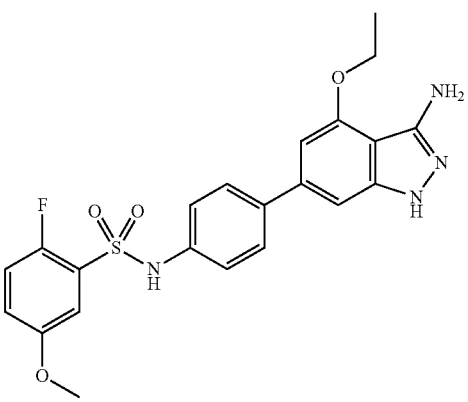
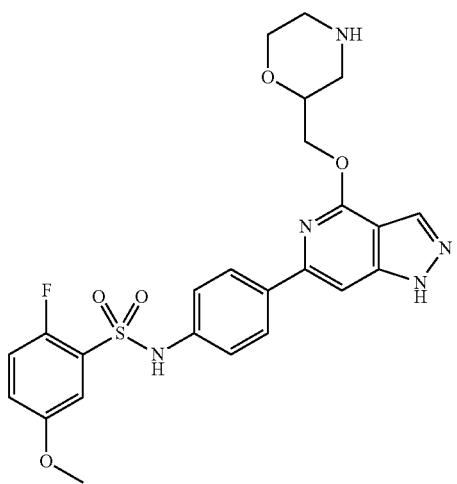 [SMILES: COc1ccc(F)c(S(=O)(=O)Nc2ccc(-c3cc4[nH]ncc4c(OCC4CNCCO4)n3)cc2)c1]
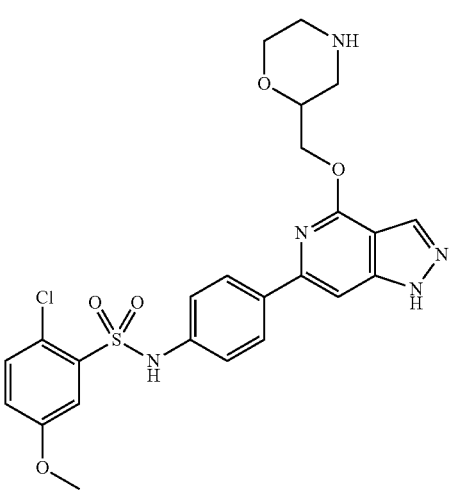 [SMILES: COc1ccc(Cl)c(S(=O)(=O)Nc2ccc(-c3cc4[nH]ncc4c(OCC4CNCCO4)n3)cc2)c1]

TABLE 1-continued

Exemplary Compounds

TABLE 1-continued
Exemplary Compounds
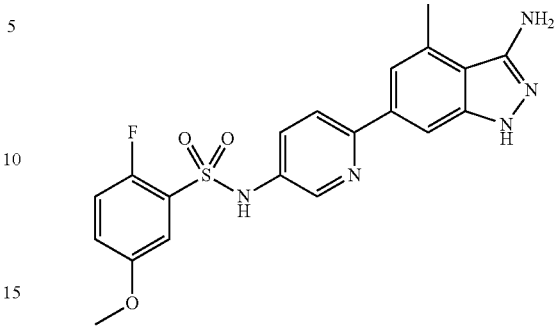
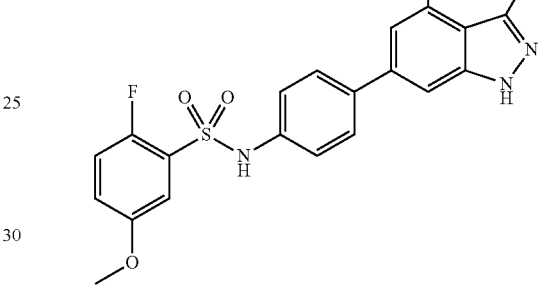
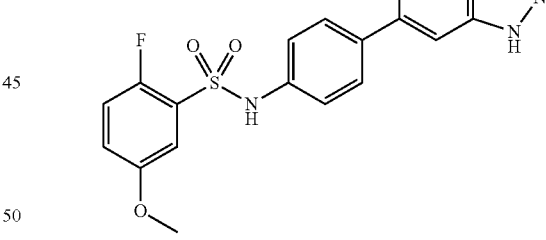
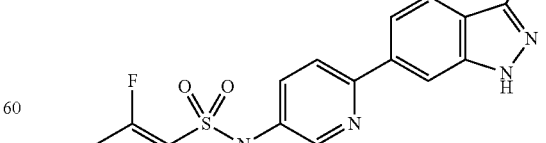
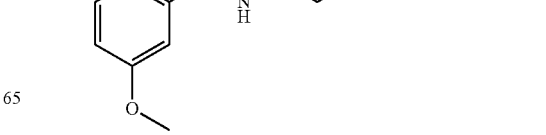

TABLE 1-continued
Exemplary Compounds
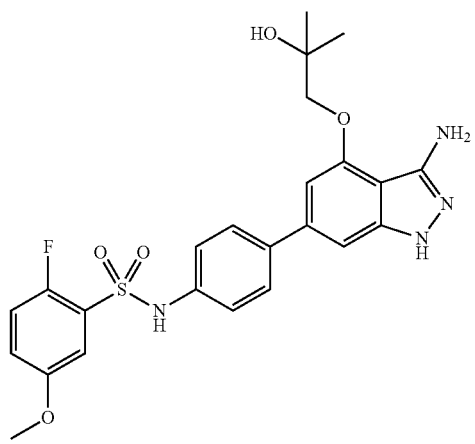 [SMILES: COc1ccc(F)c(S(=O)(=O)Nc2ccc(-c3cc(OCC(C)(C)O)c4c(N)n[nH]c4c3)cc2)c1]
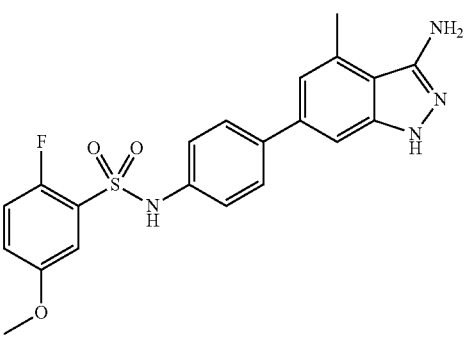
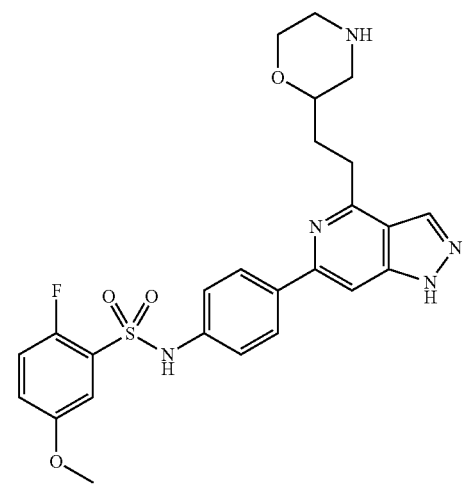 [SMILES: COc1ccc(F)c(S(=O)(=O)Nc2ccc(-c3cc4[nH]ncc4c(CCC4CNCCO4)n3)cc2)c1]
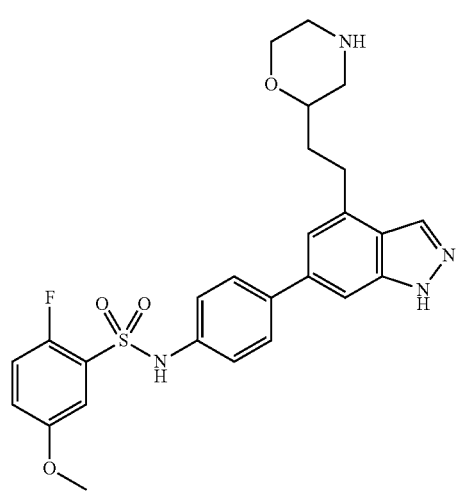
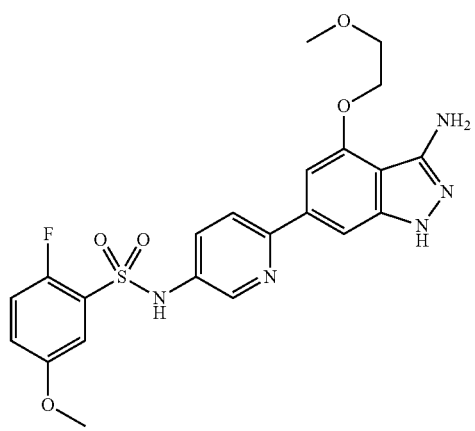 [SMILES: COCCOc1cc(-c2ccc(NS(=O)(=O)c3cc(OC)ccc3F)cn2)cc2[nH]nc(N)c12]
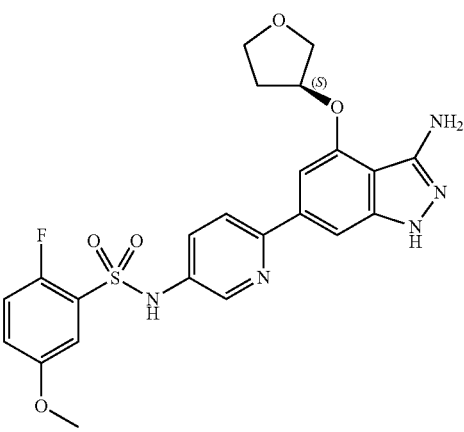

TABLE 1-continued
Exemplary Compounds
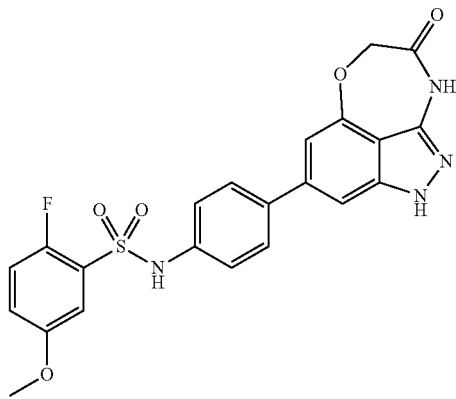 [SMILES: COc1ccc(F)c(S(=O)(=O)Nc2ccc(-c3cc4c5c(n[nH]c5c3)NC(=O)CO4)cc2)c1]
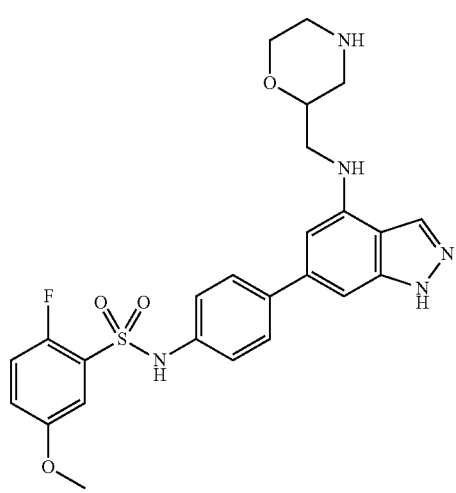 [SMILES: COc1ccc(F)c(S(=O)(=O)Nc2ccc(-c3cc(NCC4CNCCO4)c4cn[nH]c4c3)cc2)c1]
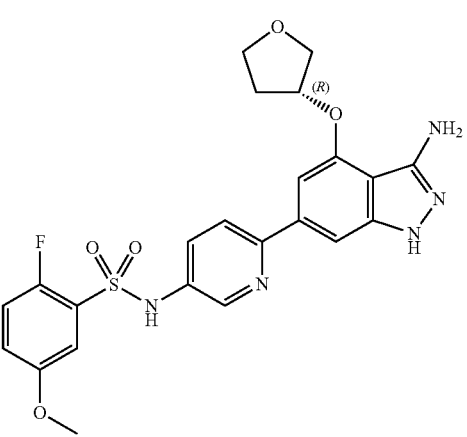
TABLE 1-continued
Exemplary Compounds
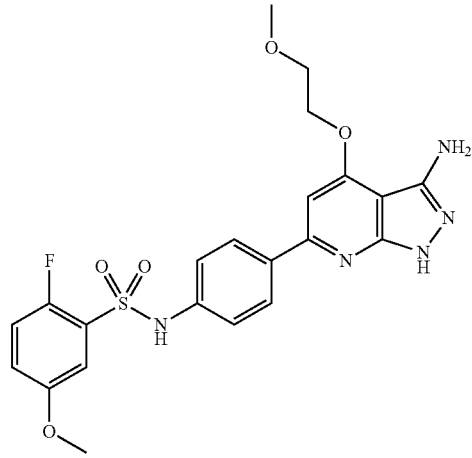 [SMILES: COCCOc1cc(-c2ccc(NS(=O)(=O)c3cc(OC)ccc3F)cc2)nc2[nH]nc(N)c12]
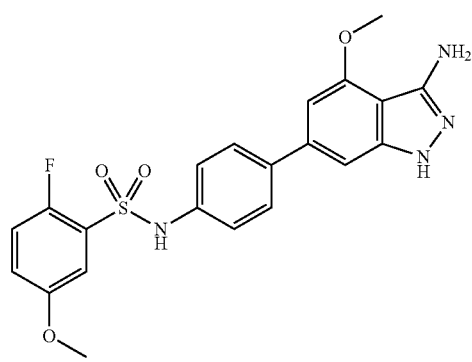 [SMILES: COc1ccc(F)c(S(=O)(=O)Nc2ccc(-c3cc(OC)c4c(N)n[nH]c4c3)cc2)c1]
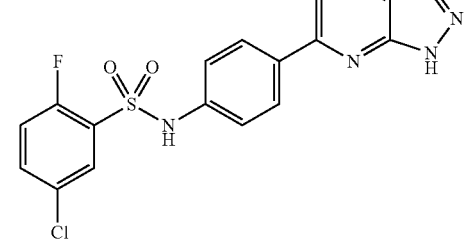
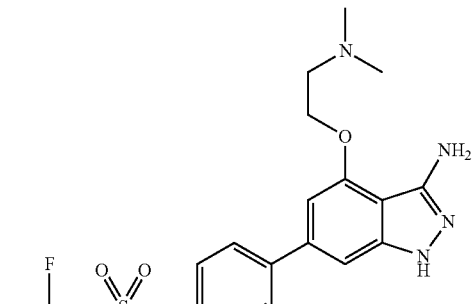

TABLE 1-continued

Exemplary Compounds

TABLE 1-continued

Exemplary Compounds

TABLE 1-continued
Exemplary Compounds
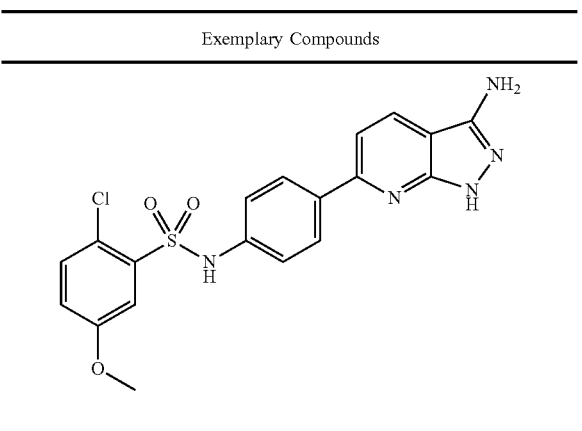
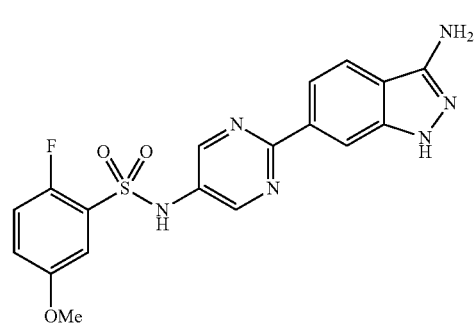 [SMILES: COc1ccc(F)c(S(=O)(=O)Nc2cnc(-c3ccc4c(N)n[nH]c4c3)nc2)c1]
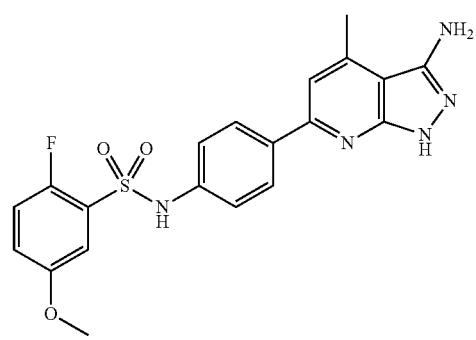 [SMILES: COc1ccc(F)c(S(=O)(=O)Nc2ccc(-c3cc(C)c4c(N)n[nH]c4n3)cc2)c1]
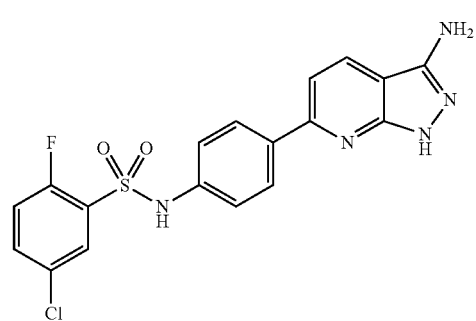 [SMILES: Nc1n[nH]c2nc(-c3ccc(NS(=O)(=O)c4cc(Cl)ccc4F)cc3)ccc12]
TABLE 1-continued
Exemplary Compounds
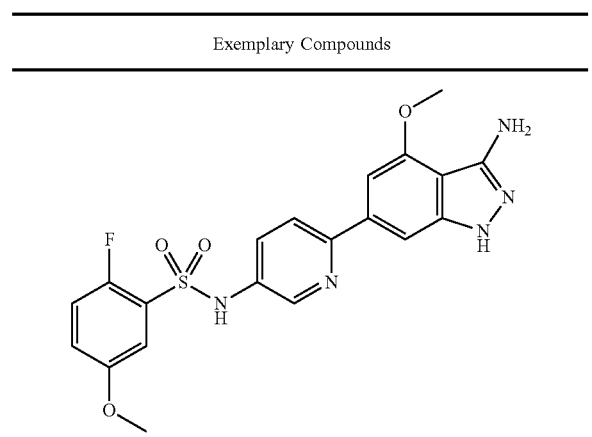
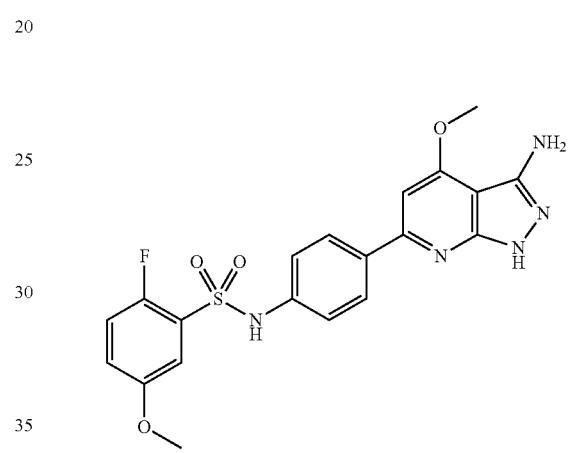
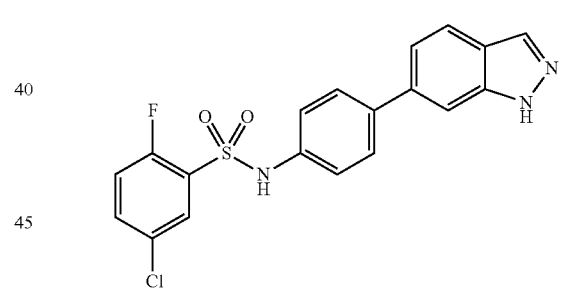
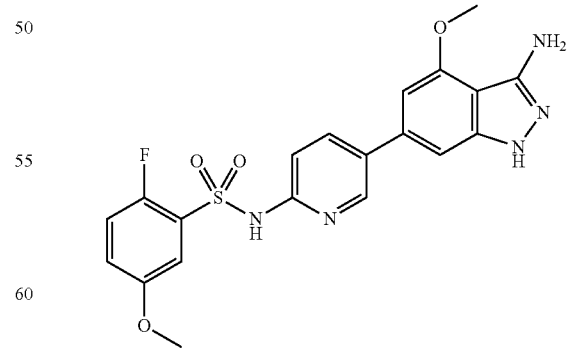
In another aspect, the invention generally relates to a pharmaceutical composition comprising an amount of a compound having the structural formula of (I):

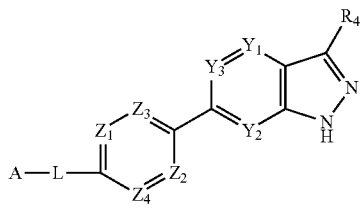

(I)

wherein,

A is an aryl group selected from the group consisting of unsubstituted 5- or 6-membered aryl groups and substituted 5- or 6-membered aryl groups;

L is a linking group comprising

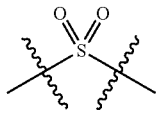 [SMILES: *S(*)(=O)=O]

$Y_1$ is $CR_1$ or N, wherein $R_1$ is a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group;

$Y_2$ is $CR_2$ or N, wherein $R_2$ is H, or a $C_1$-$C_6$ alkyl group;
$Y_3$ is $CR_3$ or N, wherein $R_3$ is H, or a $C_1$-$C_6$ alkyl group;
each of $Z_1$, $Z_2$, $Z_3$ and $Z_4$ is independently selected from the group consisting of CR and N, wherein R is H or a $C_1$-$C_6$ alkyl group; and $R_4$ is H, a $C_1$-$C_6$ alkyl group, —N(R')R", —N(R')—C(O)R", —N(R')—C(O)—NH—R", R'—O—R", wherein each of R' and R" is independently selected from the group consisting of H and a $C_1$-$C_6$ alkyl group, wherein $R_4$ and $Y_1$ optionally may join together to form a 5- to 8-membered ring, or a pharmaceutically acceptable form thereof, effective to treat, prevent, or reduce one or more diseases or disorders, in a mammal, including a human, and a pharmaceutically acceptable excipient, carrier, or diluent.

Pharmaceutical compositions of the invention may be used to effectively treat, prevent, or reduce various diseases and conditions, including one or more of autoimmune diseases, cancer, cardiovascular diseases, inflammatory diseases and diabetes, or a related disease or disorder thereof.

In certain embodiments, the pharmaceutical composition of the invention is effective to treat, prevent, or reduce an autoimmune disease or disorder.

In certain embodiments, the pharmaceutical composition of the invention is effective to treat, prevent, or reduce cancer, or a related disease or disorder.

In certain embodiments, the pharmaceutical composition of the invention is effective to treat, prevent, or reduce a cardiovascular disease or disorder.

In certain embodiments, the pharmaceutical composition of the invention is effective to treat, prevent, or reduce an inflammatory disease or disorder.

In certain embodiments, the pharmaceutical composition of the invention is effective to treat, prevent, or reduce diabetes, or a related disease or disorder.

In yet another aspect, the invention relates to a unit dosage form comprising a pharmaceutical composition disclosed herein.

In yet another aspect, the invention relates to a method for treating, reducing, or preventing a disease or disorder, comprising administering to a subject in need thereof a pharmaceutical composition comprising a compound having the structural formula of (I):

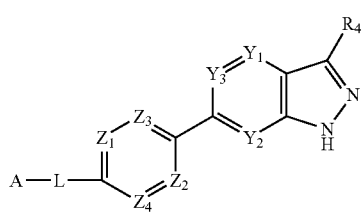

(I)

wherein,

A is an aryl group selected from the group consisting of unsubstituted 5- or 6-membered aryl groups and substituted 5- or 6-membered aryl groups;

L is a linking group comprising

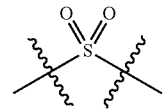 [SMILES: *S(*)(=O)=O]

$Y_1$ is $CR_1$ or N, wherein $R_1$ is a hydrogen, or a $C_1$-$C_6$ alkyl group, —O—$R_h$, —S—$R_h$, —N(R')$R_h$, wherein R' is selected from the group consisting of H and a $C_1$-$C_6$ alkyl group and $R_h$ is a hydrocarbyl group;

$Y_2$ is $CR_2$ or N, wherein $R_2$ is H, or a $C_1$-$C_6$ alkyl group;
$Y_3$ is $CR_3$ or N, wherein $R_3$ is H, or a $C_1$-$C_6$ alkyl group;
each of $Z_1$, $Z_2$, $Z_3$ and $Z_4$ is independently selected from the group consisting of CR and N, wherein R is H or a $C_1$-$C_6$ alkyl group; and $R_4$ is H, a $C_1$-$C_6$ alkyl group, —N(R')R", —N(R')—C(O)R", —N(R')—C(O)—NH—R", R'—O—R", wherein each of R' and R" is independently selected from the group consisting of H and a $C_1$-$C_6$ alkyl group, wherein $R_4$ and $Y_1$ optionally may join together to form a 5- to 8-membered ring, or a pharmaceutically acceptable form thereof, effective to treat, prevent, or reduce one or more of autoimmune disease or disorder, cancer, a cardiovascular disease or disorder, inflammatory disease or disorder and diabetes, or a related disease or disorder thereof, in a mammal, including a human, and a pharmaceutically acceptable excipient, carrier, or diluent.

Therapeutic methods of the invention may be used to effectively treat, prevent, or reduce various diseases and conditions, including one or more of autoimmune diseases, cancer, cardiovascular diseases, inflammatory diseases and diabetes, or a related disease or disorder thereof.

In certain embodiments, the method of the invention is for treating, preventing, or reducing an autoimmune disease or disorder.

In certain embodiments, the method of the invention is for treating, preventing, or reducing cancer, or a related disease or disorder.

In certain embodiments, the method of the invention is for treating, preventing, or reducing a cardiovascular disease or disorder.

In certain embodiments, the method of the invention is for treating, preventing, or reducing an inflammatory disease or disorder.

In certain embodiments, the method of the invention is for treating, preventing, or reducing diabetes, or a related disease or disorder.

In yet another aspect, the invention relates to effectively inhibition of serum and glucocorticoid-regulated kinase (SGK) 1 and/or 2 by administering to a subject in need thereof an SGK inhibitor disclosed herein.

In yet another aspect, the invention relates to effectively inhibition of serum and glucocorticoid-regulated kinase (SGK) 1 and/or 2 by administering to a subject in need thereof a pharmaceutical composition comprising an SGK inhibitor disclosed herein.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES

Compound Syntheses

I. Preparation of 2-fluoro-5-methoxy-N-(4-(4-(morpholin-2-ylmeth-oxy)-1H-pyrazolo[3,4-b]pyridin-6-yl)phenyl)benzenesulfonamide (A)

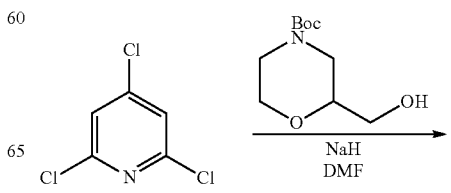

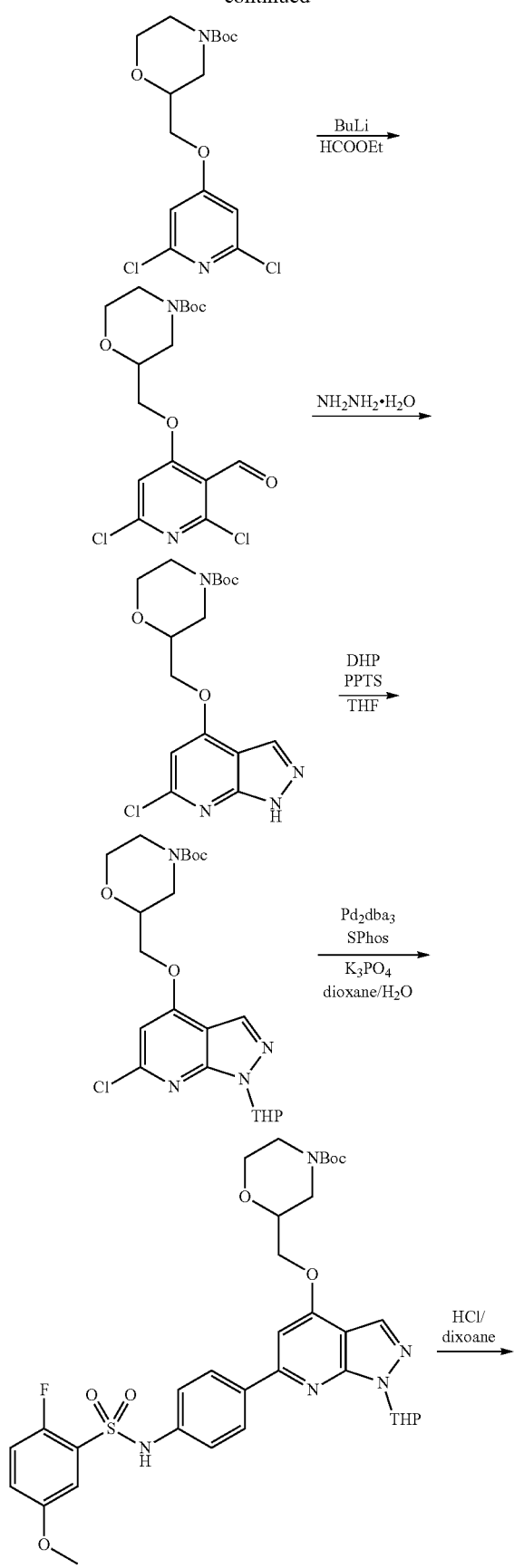

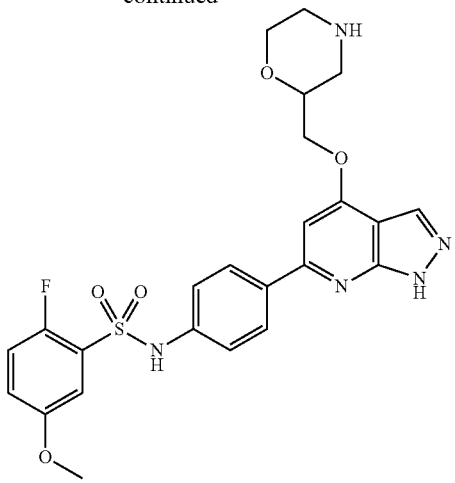

1. Preparation of tert-butyl 2-(((2,6-dichloropyridin-4-yl)oxy)-methyl)morpholine-4-carboxylate To a solution of tert-butyl 2-(hydroxymethyl)morpholine-4-carboxylate (2.17 g, 10 mmol) in THF, cooled in ice bath, was added NaH (60%, 400 mg, 10 mmol). The mixture was allowed to warm to room temperature, stirred for 30 min, and recooled in ice-water bath, followed by the addition of 2,4,6-trichloropyridine (1.82 g, 10 mmol). The reaction mixture was allowed to warm to room temperature (rt), stirred for 0.5 h, quenched with saturated aqueous NH$_4$Cl solution, and extracted with EtOAc (100 mL). The organic phase were collected, washed with water (50 mL×5), dried over Na$_2$SO$_4$, and concentrated. The residue was purified by FCC (Petroleum ether:EtOAc=10:1) to give the title compound as a colorless oil, which solidified upon standing at room temperature overnight (2.1 g, yield: 58%).

2. Preparation of tert-butyl 2-(((2,6-dichloro-3-formylpyridin-4-yl)oxy)methyl)morpholine-4-carboxylate A solution of tert-butyl 2-(((2,6-dichloropyridin-4-yl)oxy)methyl)-morpholine-4-carboxylate (2.0 g, 5.5 mmol) in THF was cooled to −78° C., and n-butyl lithium (2.5M, 2.2 mL, 5.5 mmol) was added dropwise via a syringe. The mixture was stirred at −78° C. for 0.5 h, followed by the addition of HCOOEt (1.22 g, 4.65 mmol). After stirred at −78° C. for 2 h, the mixture was quenched with saturated aqueous NH$_4$Cl (30 mL) and extracted with EtOAc (100 mL). The organic phase was collected, washed with brine (30 mL×2), dried over Na$_2$SO$_4$, and concentrated to give the crude title compound, which was used in the next step without any further purification.

3. Preparation of tert-butyl 2-(((6-chloro-1H-pyrazolo[3,4-b]-pyridin-4-yl)oxy)methyl)morpholine-4-carboxylate The previous crude compound was dissolved in EtOH (20 mL) and hydrazine hydrate (825 mg, 16.5 mmol) was added. The resultant mixture was stirred at 100° C. in a capped vial for 0.5 h. TLC indicated the reaction was complete. The mixture was concentrated. The residue was taken up in EtOAc (100 mL), washed with water (20 mL×2), dried over Na$_2$SO$_4$, and concentrated. The residue was purified by FCC (petroleum ether:EtOAc=1:1) to give a light yellow foam (500 mg, yield: 24% (two steps)).

4. Preparation of tert-butyl 2-(((6-chloro-1-(tetrahydro-2H-pyran-2-yl)-1H-pyrazolo[3,4-b]pyridin-4-yl)oxy)methyl)morpholine-4-carboxylate To a solution of tert-butyl 2-(((6-chloro-1H-pyrazolo[3,4-b]pyridin-4-yl)oxy)methyl)morpholine-4-carboxylate (500 mg, 1.356 mmol) in THF (5 mL) were added PPTS (34 mg, 0.136 mmol) and DHP (125 mg, 1.491 mmol). The mixture was stirred at 60° C. for 1 h. TLC indicated the reaction was complete. The mixture was concentrated and the residue was purified by FCC (petroleum ether:EtOAc=5:1) to give the title compound (316 mg, yield: 52%).

5. Preparation of tert-butyl 2-(((6-(4-(2-fluoro-5-methoxyphenyl-sulfonamido)phenyl)-1-(tetrahydro-2H-pyran-2-yl)-1H-pyrazolo[3,4-b]pyridin-4-yl)oxy)methyl)morpholine-4-carboxylate A solution of tert-butyl 2-(((6-chloro-1-(tetrahydro-2H-pyran-2-yl)-1H-pyrazolo[3,4-b]pyridin-4-yl)oxy)methyl)morpholine-4-carboxylate (100 mg, 0.221 mmol), 2-fluoro-5-methoxy-N-(4-(4,4,5,5-tetramethyl-1,3,2-dioxaborolan-2-yl)phenyl)benzenesulfonamide (94 mg, 0.232 mmol), Pd$_2$dba$_3$ (20 mg, 0.0221 mmol), SPhos (36 mg, 0.0884 mmol), and 5M aqueous K$_3$PO$_4$ (0.3 mL, 1.105 mmol) in dioxane (2 mL) was stirred at 110° C. overnight. LCMS indicated the reaction was complete. The mixture was poured into water (10 mL) and extracted with DCM (30 mL). The organic layer was collected, washed with water (15 mL×2), dried over Na$_2$SO$_4$, and concentrated. The residue was purified by FCC (petroleum ether:EtOAc=5:1 to 3:1) to give the title compound (130 mg, yield: 84%).

6. Preparation of 2-fluoro-5-methoxy-N-(4-(4-(morpholin-2-ylmeth-oxy)-1H-pyrazolo[3,4-b]pyridin-6-yl)phenyl)benzenesulfonamide To a solution of tert-butyl 2-(((6-(4-(2-fluoro-5-methoxy-phenylsulfon-amido)phenyl)-1-(tetrahydro-2H-pyran-2-yl)-1H-pyrazolo[3,4-b]pyridin-4-yl)oxy)methyl)morpholine-4-carboxylate (130 mg, 0.186 mmol) in 4M HCl/dioxane (2 mL) was added iPrOH (1 mL). The mixture was stirred at room temperature for 2 h. LCMS indicated the reaction was complete. The mixture was adjusted with 2M NaOH to PH=78, and extracted with DCM (30 mL). The organic phase was partitioned and concentrated. The residue was purified by Prep-TLC (DCM:MeOH=10:1) to give title compound (60 mg, yield: 63%). MS-ESI: 513.2 (M+1)$^+$, $^1$H NMR (400 MHz, cd$_3$od) δ 8.09 (s, 1H), 7.96 (d, J=8.9 Hz, 2H), 7.34 (dd, J=5.6, 3.0 Hz, 1H), 7.26 (d, J=8.8 Hz, 2H), 7.19-7.09 (m, 2H), 7.07 (s, 1H), 4.46 (d, J=4.5 Hz, 2H), 4.32-4.21 (m, 1H), 4.14-4.10 (m, 1H), 3.97-3.88 (m, 1H), 3.77 (s, 3H), 3.53-3.48 (m, 1H), 3.25-3.19 (m, 3H).

II. Preparation of 2-fluoro-5-methoxy-N-(4-(4-(morpholin-2-ylmeth-oxy)-1H-pyrazolo[4,3-c]pyridin-6-yl)phenyl)benzenesulfonamide (B)

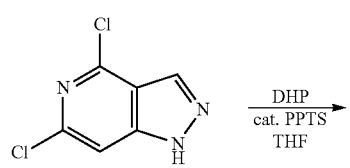

1. Preparation of 4,6-dichloro-1-(tetrahydro-2H-pyran-2-yl)-1H-pyrazolo[4,3-c]pyridine To a solution of 4,6-dichloro-1H-pyrazolo[4,3-c]pyridine (360 mg, 1.91 mmol) in THF (5 mL) were added PPTS (24 mg, 0.095 mmol) and DHP (0.8 mL). The mixture was stirred at 60° C. for 2 h. TLC indicated the reaction was complete. The mixture was concentrated and the residue was

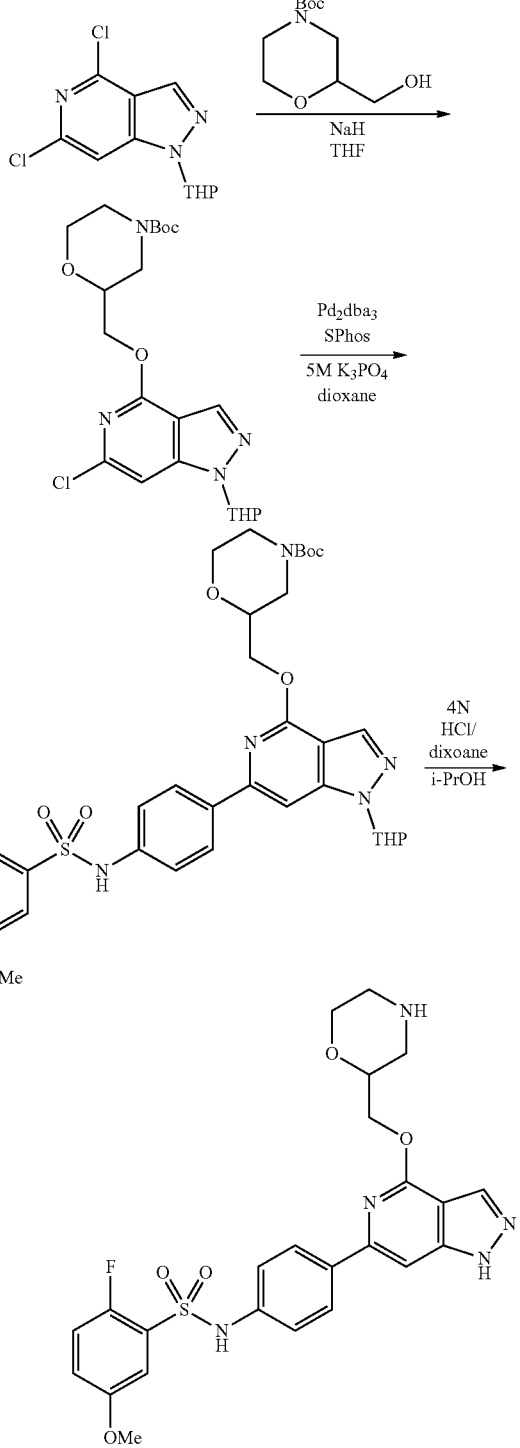

purified by FCC (petroleum ether:EtOAc=10:1) to give the title compound (465 mg, yield: 89%).

2. Preparation of tert-butyl 2-(((6-chloro-1-(tetrahydro-2H-pyran-2-yl)-1H-pyrazolo[4,3-c]pyridin-4-yl)oxy)methyl)morpholine-4-carboxylate To a solution of tert-butyl 2-(hydroxymethyl)morpholine-4-carboxylate (158 mg, 0.73 mmol) in THF, cooled in ice bath, was added NaH (60%, 34 mg, 0.84 mmol). The mixture was allowed to warm to room temperature, stirred for 30 min, and recooled in ice-water bath, followed by the addition of 4,6-dichloro-1-(tetrahydro-2H-pyran-2-yl)-1H-pyrazolo[4,3-c]pyridine (200 mg, 0.73 mmol). The reaction mixture was allowed to warm to rt, stirred for overnight, diluted with water, and extracted with EtOAc (100 mL). The organic phase were collected, washed with water (50 mL×5), dried over Na$_2$SO$_4$, and concentrated. The residue was purified by FCC (Petroleum ether:EtOAc=2:1) to give the title compound (258 mg, yield: 78%).

3. Preparation of tert-butyl 2-(((6-(4-(2-fluoro-5-methoxyphenylsulf-onamido)phenyl)-1-(tetrahydro-2H-pyran-2-yl)-1H-pyrazolo[4,3-c]pyridin-4-yl)oxy)methyl)morpholine-4-carboxylate A solution of tert-butyl 2-(((6-chloro-1-(tetrahydro-2H-pyran-2-yl)-1H-pyrazolo[4,3-c]pyridin-4-yl)oxy)methyl)morpholine-4-carboxylate (50 mg, 0.11 mmol), 2-fluoro-5-methoxy-N-(4-(4,4,5,5-tetramethyl-1,3,2-dioxaborolan-2-yl)phenyl)benzenesulfonamide (47 mg, 0.11 mmol), Pd$_2$dba$_3$ (10 mg, 0.011 mmol), SPhos (18 mg, 0.044 mmol), and 5M aqueous K$_3$PO$_4$ (0.3 mL) in dioxane (2 mL) was stirred at 110° C. overnight. LCMS indicated the reaction was complete. The mixture was poured into water (10 mL) and extracted with EA (30 mL). The organic layer was collected, washed with water (15 mL×2), dried over Na$_2$SO$_4$, and concentrated. The residue was purified by FCC (petroleum ether:EtOAc=2:1 to 1:2) to give the title compound (67 mg, yield: 87%).

4. Preparation of 2-fluoro-5-methoxy-N-(4-(4-(morpholin-2-ylme-thoxy)-1H-pyrazolo[4,3-c]pyridin-6-yl)phenyl)benzenesulfonamide To a solution of tert-butyl 2-(((6-(4-(2-fluoro-5-methoxy-phenylsulfona-mido)-phenyl)-1-(tetrahydro-2H-pyran-2-yl)-1H-pyrazolo[4,3-c]pyridin-4-yl)oxy)methyl)morpholine-4-carboxylate (67 mg, 0.09 mmol) in 4M HCl/dioxane (1 mL) was added iPrOH (1 mL). The mixture was stirred at room temperature for 2 h. LCMS indicated the reaction was complete. The mixture was adjusted with 2M NaOH to PH=7~8, and extracted with DCM (30 mL). The organic phase was partitioned and concentrated. The residue was purified by Prep-TLC (DCM:MeOH=10:1) to give the title compound (20 mg, yield: 43%). MS-ESI: 514.2 (M+1)$^+$, $^1$H NMR (400 MHz, DMSO) δ 13.46 (s, 1H), 8.09 (s, 1H), 7.99 (d, J=8.8 Hz, 2H), 7.50 (s, 1H), 7.33 (d, J=9.4 Hz, 1H), 7.31-7.26 (m, 1H), 7.21-7.15 (m, 3H), 4.49 (d, J=4.4 Hz, 2H), 3.81 (d, J=11.8 Hz, 1H), 3.75 (s, 3H), 3.54 (dd, J=11.5, 8.8 Hz, 2H), 2.87-2.63 (m, 4H).

III. Preparation of N-(4-(3-amino-4-methoxy-1H-indazol-6-yl)-phenyl)-2-fluoro-5-methoxybenzenesulfonamide (C)

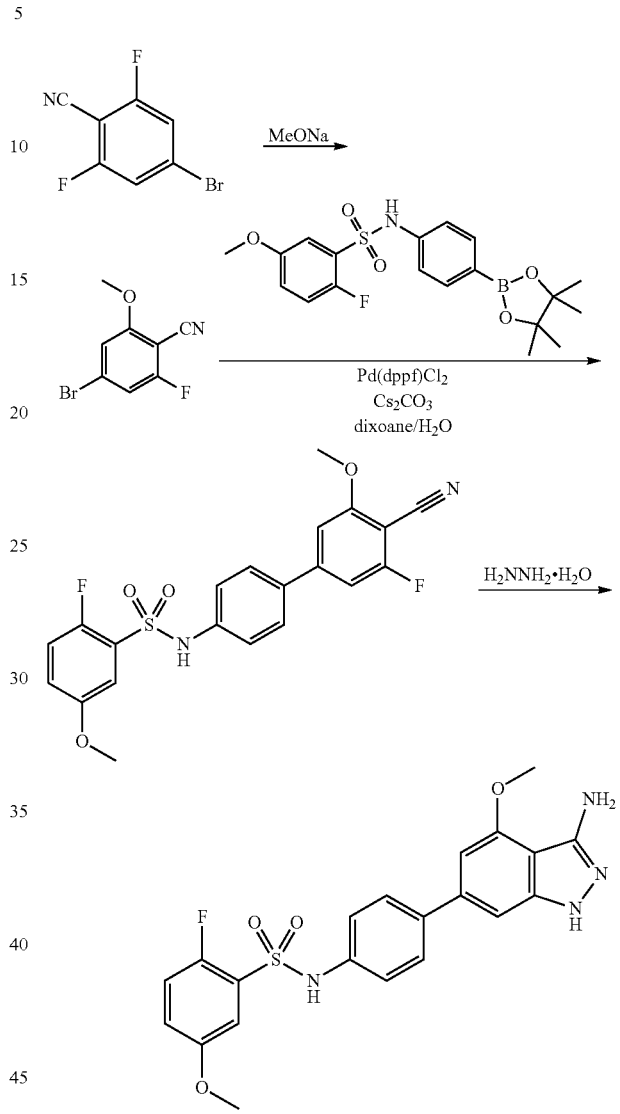

1. Preparation of 4-bromo-2-fluoro-6-methoxybenzonitrile

To a solution of 4-bromo-2,6-difluorobenzonitrile (218 mg, 1.0 mmol) in THF (8 mL) at 0° C. was slowly added sodium methoxide (65 mg, 1.2 mmol) and the mixture was stirred at room temperature for 16 h. The mixture was concentrated and partitioned between EtOAc (30 mL) and water (15 mL). The organic extracts were dried (Na$_2$SO$_4$), filtered, and concentrated. The residue was purified by silica gel chromatography eluting with ethyl acetate in hexane (0-5 percent) to afford the title compound (90 mg, yield: 39%).

2. Preparation of N-(4'-cyano-3'-fluoro-5'-methoxy-[1,1'-biphenyl]-4-yl)-2-fluoro-5-methoxybenzenesulfonamide A mixture of 4-bromo-2-fluoro-6-methoxybenzonitrile (90 mg, 0.39 mmol), 2-fluoro-5-methoxy-N-(4-(4,4,5,5-tetramethyl-1,3,2-dioxaborolan-2-yl)phenyl)benzenesulfonamide (275 mg, 0.43 mmol), Pd(dppf)Cl$_2$.DCM (32 mg, 0.039 mmol) and Cs$_2$CO$_3$ (252 mg, 0.78 mmol) in dioxane (8 mL) and H$_2$O (0.5 mL) was heated under N$_2$ at 90° C. for 18 h. The mixture was cooled to room temperature, diluted with EtOAc (30 mL), filtered through celite, concentrated and purified by silica gel chromatography eluting with ethyl acetate in hexane (0-30 percent) to afford the title compound (130 mg, yield: 80%).

3. Preparation of N-(4-(3-amino-4-methoxy-1H-indazol-6-yl)phenyl)-2-fluoro-5-methoxybenzenesulfonamide To a solution of N-(4'-cyano-3'-fluoro-5'-methoxy-[1,1'-biphenyl]-4-yl)-2-fluoro-5-methoxybenzenesulfonamide (130 mg, 0.3 mmol) in EtOH (8 mL) was added 85% hydrazine hydrate (1 mL). The mixture was heated to 100° C. in a capped vial for 16 h. The reaction mixture was cooled to rt, diluted with EtOAc (30 mL), washed with water (5 mL), dried over Na$_2$SO$_4$ and concentrated. The residue was purified by prep-TLC to give the title compound (60 mg, yield: 45%). MS-ESI: 443.2 (M+1)$^+$, $^1$H NMR (400 MHz, DMSO) δ 11.40 (s, 1H), 10.71 (s, 1H), 7.56 (d, J=8.6 Hz, 2H), 7.34 (t, J=9.4 Hz, 1H), 7.27 (dd, J=5.6, 3.2 Hz, 1H), 7.21 (t, J=3.5 Hz, 1H), 7.17 (d, J=8.6 Hz, 2H), 6.86 (d, J=0.7 Hz, 1H), 6.46 (d, J=0.6 Hz, 1H), 4.95 (s, 2H), 3.88 (s, 3H), 3.75 (s, 3H).

IV. Preparation of N-(4-(3-amino-4-methyl-1H-pyrazolo[4,3-c]pyridin-6-yl)phenyl)-2-fluoro-5-methoxybenzenesulfonamide (D)

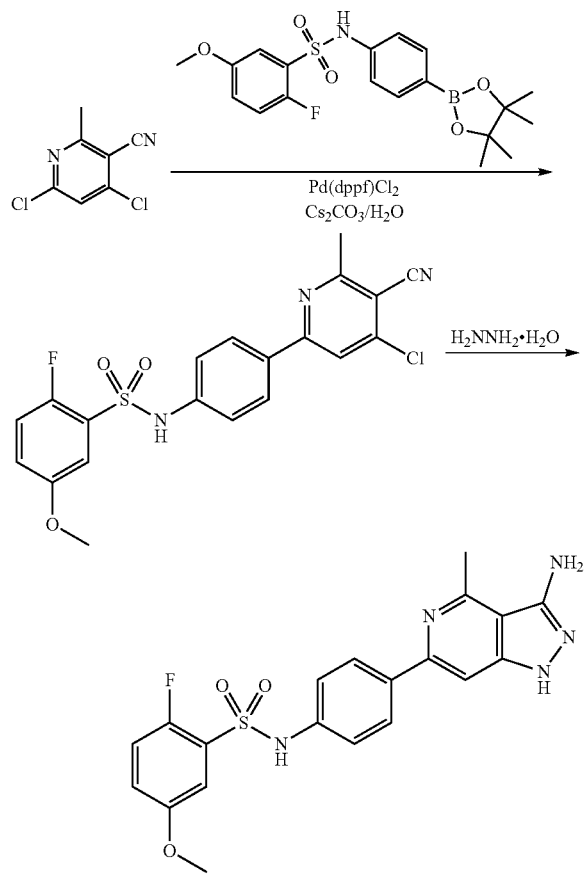

1. Preparation of N-(4-(4-chloro-5-cyano-6-methylpyridin-2-yl)phenyl)-2-fluoro-5-methoxybenzenesulfonamide A mixture of 4,6-dichloro-2-methylnicotinonitrile (100 mg, 0.53 mmol), 2-fluoro-5-methoxy-N-(4-(4,4,5,5-tetramethyl-1,3,2-dioxaborolan-2-yl)phenyl)benzenesulfonamide (218 mg, 0.53 mmol), Pd(dppf)Cl$_2$.DCM (43 mg, 0.053 mmol) and Cs$_2$CO$_3$ (348 mg, 1.06 mmol) in dioxane (5 mL) and H$_2$O (0.8 mL) was heated under N$_2$ at 90° C. for 16 h. The mixture was cooled to room temperature, diluted with EtOAc (30 mL), filtered through celite, concentrated and purified by silica gel chromatography eluting with ethyl acetate in hexane (10-50 percent) to afford the title compound (150 mg, yield: 55%).

2. Preparation of N-(4-(3-amino-4-methyl-1H-pyrazolo[4,3-c]pyridin-6-yl)phenyl)-2-fluoro-5-methoxybenzenesulfonamide To a solution of N-(4-(4-chloro-5-cyano-6-methylpyridin-2-yl)phenyl)-2-fluoro-5-methoxybenzenesulfonamide (150 mg, 0.34 mmol) in n-butanol (3 mL) was added 85% hydrazine hydrate (70 mg, 6 eq.). The mixture was heated to 130° C. in a capped vial for 16 h. The reaction mixture was cooled to rt, diluted with EtOAc (30 mL), washed with water (5 mL), dried over Na$_2$SO$_4$ and concentrated. The residue was purified by prep-TLC to give the title compound (75 mg, yield: 48%). MS-ESI: 428.3 (M+1)$^+$, $^1$H NMR (400 MHz, DMSO) δ 11.90 (s, 1H), 10.75 (s, 1H), 7.97 (d, J=8.6 Hz, 2H), 7.37 (dd, J=16.0, 6.5 Hz, 2H), 7.30 (dd, J=5.5, 3.2 Hz, 1H), 7.22 (dd, J=9.1, 6.2 Hz, 3H), 5.33 (s, 2H), 3.78 (s, 3H), 2.75 (s, 3H).

V. Preparation of N-(4-(3-amino-4-methyl-1H-pyrazolo[3,4-b]-pyridin-6-yl)phenyl)-2-fluoro-5-methoxybenzenesulfonamide (E)

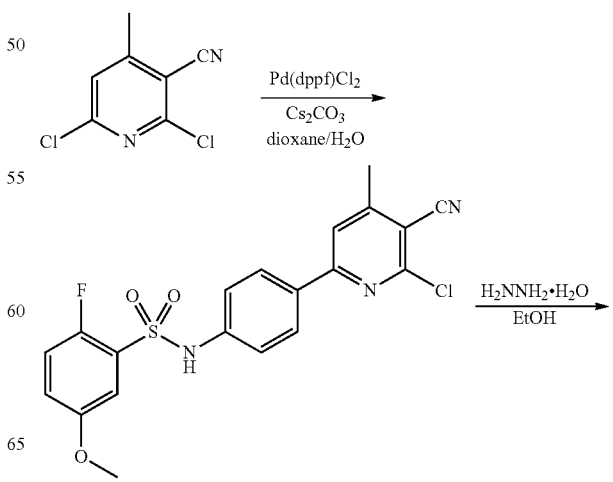

-continued

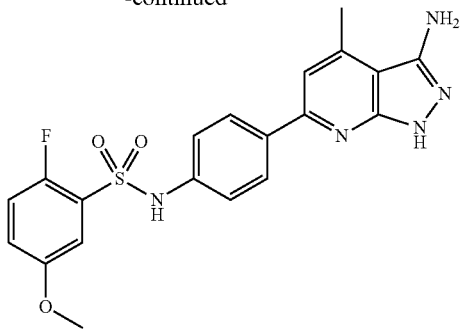

1. Preparation of N-(4-(6-chloro-5-cyano-4-methylpyridin-2-yl)phenyl)-2-fluoro-5-methoxybenzenesulfonamide A mixture of 2,6-dichloro-4-methylnicotinonitrile (100 mg, 0.54 mmol), 2-fluoro-5-methoxy-N-(4-(4,4,5,5-tetramethyl-1,3,2-dioxaborolan-2-yl)phenyl)benzenesulfonamide (241 mg, 0.59 mmol), Pd(dppf)Cl$_2$.DCM (44 mg, 0.054 mmol) and Cs$_2$CO$_3$ (352 mg, 1.08 mmol) in dioxane (8 mL) and H$_2$O (0.5 mL) was heated under N$_2$ at 90° C. for 18 h. The mixture was cooled to room temperature, diluted with EtOAc (30 mL), filtered through celite, concentrated and purified by silica gel chromatography eluting with ethyl acetate in hexane (0-30 percent) to afford the title compound (180 mg, yield: 78%).

2. Preparation of N-(4-(3-amino-4-methyl-1H-pyrazolo[3,4-b]pyridin-6-yl)phenyl)-2-fluoro-5-methoxybenzenesulfonamide To a solution of N-(4-(6-chloro-5-cyano-4-methylpyridin-2-yl)phenyl)-2-fluoro-5-methoxybenzenesulfonamide (180 mg, 0.42 mmol) in EtOH (10 mL) was added 85% hydrazine hydrate (1.5 mL). The mixture was heated to 100° C. in a capped vial for 8 h. The reaction mixture was cooled to room temperature and concentrated. The residue was triturated with methanol to give a title compound (18 mg, yield: 10%). MS-ESI: 428.3 (M+1)$^+$, $^1$H NMR (400 MHz, DMSO) δ 11.94 (s, 1H), 10.80 (b, 1H), 7.98 (d, J=8.4 Hz, 2H), 7.32 (m, 2H), 7.22 (m, 4H), 5.18 (s, 2H), 3.79 (s, 3H), 2.64 (s, 3H).

VI. Preparation of N-(4-(3-amino-4-methoxy-1H-pyrazolo[3,4-b]pyridin-6-yl)phenyl)-2-fluoro-5-methoxybenzenesulfonamide (F)

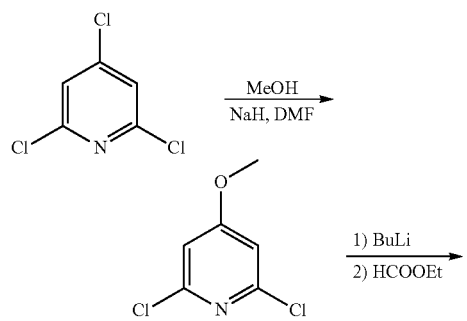

-continued

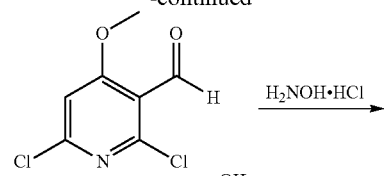

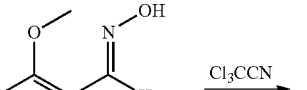

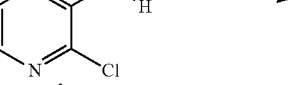

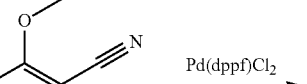

1. Preparation of 2,6-dichloro-4-methoxyypyridine

To a solution of 2,4,6-trichloropyridine (3.64 g, 20.0 mmol) in DMF (20 mL) at 0° C. were slowly added NaH (60% in mineral oil, 840 mg, 21 mmol) and MeOH (673 mg, 21 mmol). The mixture was stirred at room temperature for 16 h. The mixture was concentrated and partitioned between EtOAc (30 mL) and water (15 mL). The organic extracts were dried (Na$_2$SO$_4$), filtered, and concentrated. The residue was purified by silica gel chromatography eluting with ethyl acetate in hexane (0-5 percent) to afford the title compound (3.0 g, yield: 94%).

2. Preparation of 2,6-dichloro-4-methoxynicotinaldehyde

To a mixture of 2,6-dichloro-4-methoxypyridine (3.49 g, 19.6 mmol) in THF (100 mL) was added n-BuLi (2.5 M, 8.63 ml, 21.56 mmol) at −78° C. The mixture was stirred at that temperature for 30 min, and ethyl formate (4.4 g, 59 mmol) was added at −78'° C. The resultant mixture was stirred at that temperature for 30 min, and saturated aqueous NH₄Cl was added to quench the reaction at −78'° C. The mixture was warmed to room temperature, extracted with EtOAc (30 mL), concentrated and purified by silica gel chromatography eluting with ethyl acetate in hexane (0-30 percent) to afford the title compound (3.3 g, yield: 53%).

3. Preparation of 2,6-dichloro-4-methoxynicotinaldehyde oxime

To a solution of 2,6-dichloro-4-methoxynicotinaldehyde (2.0 g, 10 mmol) in THF (40 mL) was added hydroxylamine hydrochloride (765 mg, 11 mmol) and DIPEA (2.0 g, 15 mmol) at 0° C. The mixture was stirred at room temperature for 2 h and diluted with EtOAc (30 mL) and water (5 mL). The organic phase was collected, dried over Na₂SO₄, and concentrated to give the crude product (3.3 g).

4. Preparation of 2,6-dichloro-4-methoxynicotinonitrile

A solution of 2,6-dichloro-4-methoxynicotinaldehyde oxime (3.3 g, 10 mmol) in CNCl₃ (30 mL) was stirred at 88° C. for 3 h. The reaction mixture was diluted with EtOAc (30 mL), washed with water (5 mL), dried over Na₂SO₄, concentrated and purified by silica gel chromatography (petroleum ether:EtOAc=4:1) to give the desired product as white solid (3.0 g, 94%).

5. Preparation of N-(4-(6-chloro-5-cyano-4-methoxypyridin-2-yl)-phenyl)-2-fluoro-5-methoxy-benzenesulfonamide A mixture of 2,6-dichloro-4-methoxynicotinonitrile (812 mg, 2 mmol), 2-fluoro-5-methoxy-N-(4-(4,4,5,5-tetramethyl-1,3,2-dioxaborolan-2-yl)phenyl)benzenesulfonamide (1.75 g, 2.2 mmol), Pd(dppf)Cl₂.DCM (160 mg, 0.1 mmol) and Cs₂CO₃ (2.6 g, 4 mmol) in dioxane (24 mL) and H₂O (4 mL) was heated under N₂ at 80° C. for 6 h. The mixture was cooled to room temperature, diluted with EtOAc (30 mL), filtered through celite, concentrated and purified by silica gel chromatography eluting with ethyl acetate in hexane (0-30 percent) to afford the crude title compound (1.0 g).

6. Preparation of N-(4-(3-amino-4-methoxy-1H-pyrazolo[3,4-b]-pyridin-6-yl)phenyl)-2-fluoro-5-methoxybenzenesulfonamide To a solution of N-(4-(6-chloro-5-cyano-4-methoxypyridin-2-yl)phenyl)-2-fluoro-5-methoxybenzenesulfonamide (1.0 g, crude) in EtOH (15 mL) was added 85% hydrazine hydrate (1.2 mL). The mixture was heated to 95° C. in a capped vial for 3 h. The reaction mixture was cooled to RT, diluted with EtOAc (30 mL), washed with water (5 mL), dried over Na₂SO₄ and concentrated. The residue was purified by prep-TLC to give the title compound (110 mg). MS-ESI: 444.2 (M+1)⁺, ¹H NMR (400 MHz, DMSO) δ11.84 (s, 1H), 10.82 (s, 1H), 7.98 (d, J=8.7 Hz, 2H), 7.38-7.26 (m, 2H), 7.20 (d, J=8.6 Hz, 3H), 6.90 (s, 1H), 5.06 (s, 2H), 3.99 (s, 3H), 3.76 (s, 3H).

VII. Preparation of N-(4-(3-amino-4-methyl-1H-indazol-6-yl)-phenyl)-2-fluoro-5-methoxybenzene-sulfonamide (G)

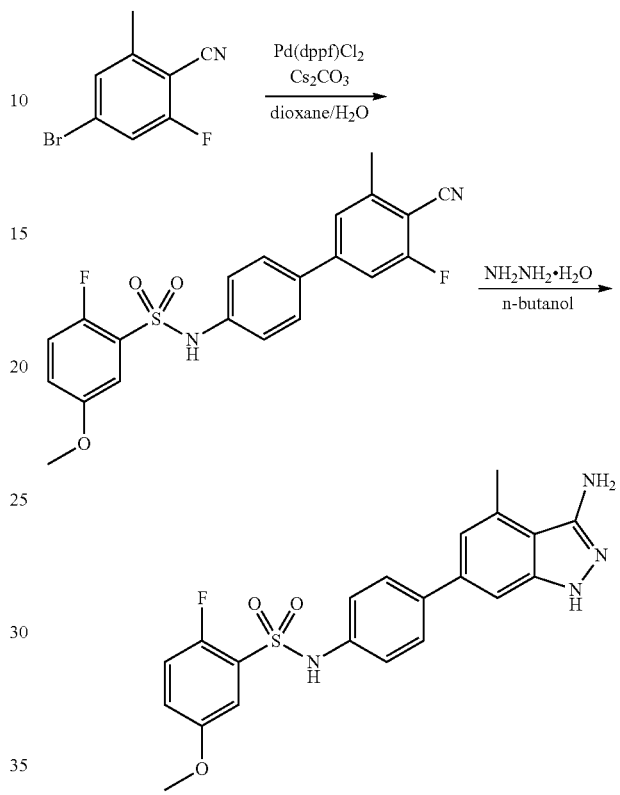

1. Preparation of N-(4'-cyano-3'-fluoro-5'-methyl-[1,1'-biphenyl]-4-yl)-2-fluoro-5-methoxybenzenesulfonamide A mixture of 4-bromo-2-fluoro-6-methylbenzonitrile (107 mg, 0.5 mmol), 2-fluoro-5-methoxy-N-(4-(4,4,5,5-tetramethyl-1,3,2-dioxaborolan-2-yl)phenyl)benzenesulfonamide (215 mg, 0.53 mmol), Pd(dppf)Cl₂.DCM (40 mg, 0.05 mmol) and Cs₂CO₃ (325 mg, 1.0 mmol) in dioxane (4 mL) and H₂O (0.5 mL) was heated under N₂ at 85° C. for 3 h. The mixture was cooled to room temperature, diluted with EtOAc (30 mL), filtered through celite, concentrated and purified by silica gel chromatography eluting with ethyl acetate in hexane (0-30 percent) to afford the title compound (170 mg, yield: 88%).

2. Preparation of N-(4-(3-amino-4-methyl-1H-indazol-6-yl)phenyl)-2-fluoro-5-methoxybenzenesulfonamide To a solution of N-(4'-cyano-3'-fluoro-5'-methyl-[1,1'-biphenyl]-4-yl)-2-fluoro-5-methoxybenzenesulfonamide (160 mg, 0.39 mmol) in EtOH (15 mL) was added 85% hydrazine hydrate (1.5 mL). The mixture was heated to 100° C. in a capped vial for 24 h. The reaction mixture was cooled to room temperature and concentrated. The residue was concentrated and purified by pre-TLC (DCM:MeOH=12:1) to give the title compound (27 mg, yield: 16%). MS-ESI: 427.2 (M+1)⁺, ¹H NMR (400 MHz, DMSO) δ 11.44 (s, 1H), 10.69 (s, 1H), 7.54 (d, J=8.6 Hz, 2H), 7.35 (t, J=9.4 Hz, 1H), 7.27 (dd, J=5.4, 3.2 Hz, 1H), 7.23-7.10 (m, 4H), 6.82 (s, 1H), 4.93 (s, 2H), 3.75 (s, 3H), 2.60 (s, 3H).

VIII. Preparation of 2-fluoro-5-methoxy-N-(4-(4-oxo-1,3,4,5-tetra-hydro-[1,4]oxazepino[5,6,7-cd]indazol-8-yl)phenyl)benzenesulfonamide (H)

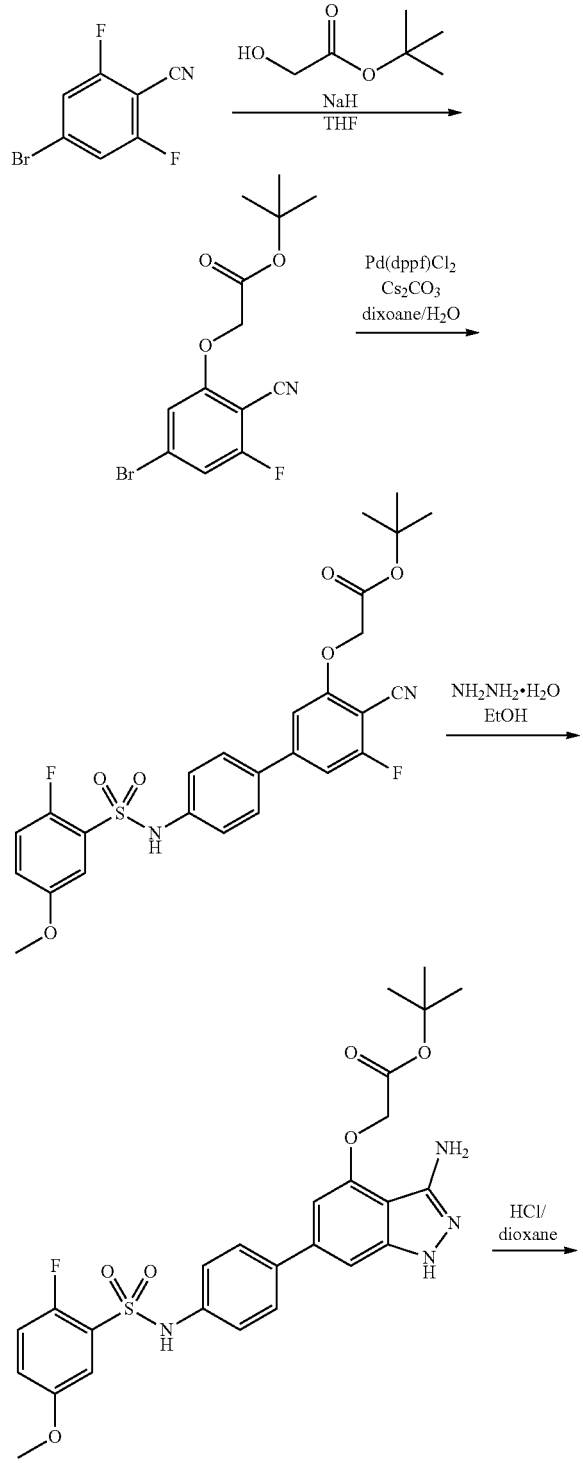

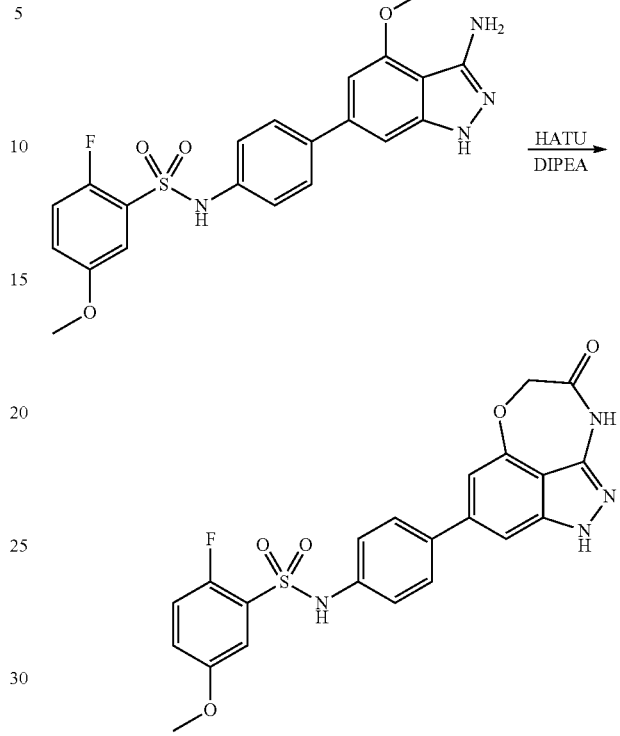

1. Preparation of tert-butyl 2-(5-bromo-2-cyano-3-fluorophenoxy)-acetate

To a solution of tert-butyl 2-hydroxyacetate (1.45 g, 11.0 mmol) in THF (15 mL), cooled to 0° C., was added sodium hydride (60% in mineral oil, 242 mg, 6.05 mmol). The mixture was warmed up to room temperature, followed by the addition of 4-bromo-2,6-difluorobenzonitrile (1.2 g, 5.5 mmol). The mixture was stirred at room temperature overnight, diluted with EtOAc (50 mL), washed with water (30 mL×3), dried over $Na_2SO_4$, and concentrated. The residue was purified by FCC (Petroleum Ether:EtOAc=40:1 to 10:1) to give the desired compound (1.4 g, yield; 77%).

2. Preparation of tert-butyl 2-((4-cyano-5-fluoro-4'-(2-fluoro-5-me-thoxyphenylsulfonamido)-[1,1'-biphenyl]-3-v)oxy)acetate A mixture of tert-butyl 2-(5-bromo-2-cyano-3-fluorophenoxy)acetate (1.55 g, 4.69 mmol), 2-fluoro-5-methoxy-N-(4-(4,4,5,5-tetramethyl-1,3,2-dioxaborolan-2-yl)phenyl)benzenesulfonamide (1.9 g, 4.69 mmol), $Pd(dppf)Cl_2.DCM$ (383 mg, 0.469 mmol) and $Cs_2CO_3$ (3.05 g, 9.38 mmol) in dioxane (25 mL) and $H_2O$ (5 mL) was heated under $N_2$ at 90° C. for 16 h. The mixture was cooled to room temperature, diluted with EtOAc (100 mL), filtered through celite, concentrated and purified by silica gel chromatography eluting with ethyl acetate in hexane (10-50 percent) to afford the title compound (2.1 g, yield: 84%).

3. Preparation of tert-butyl 2-((3-amino-6-(4-(2-fluoro-5-methoxy-phenylsulfonamido)phenyl)-1H-indazol-4-yl)oxy)acetate To a solution of tert-butyl 2-((4-cyano-5-fluoro-4'-(2-fluoro-5-methoxy-phenylsulfonamido)-[1,1'-biphenyl]-3- yl)oxy)acetate (1.8 g, 3.39 mmol) in n-butanol (15 mL) was added 98% hydrazine hydrate (543 mg, 5 eq.). The mixture was heated to 105° C. in a capped vial for 16 h. The reaction mixture was cooled to rt, diluted with EtOAc (30 mL), washed with water (5 mL), dried over Na₂SO₄ and concentrated. The residue was purified by silica gel chromatography eluting with dichloromethane in methyl alcohol (10 percent) to afford the title compound (890 mg, yield: 43%).

4. Preparation of 2-((3-amino-6-(4-(2-fluoro-5-methoxyphenyl-sulfonamido)phenyl)-1H-indazol-4-yl)oxy)acetic acid A solution of tert-butyl 2-((3-amino-6-(4-(2-fluoro-5-methoxyphenylsulfon-amido)phenyl)-1H-indazol-4-yl)oxy) acetate (890 mg, 1.64 mmol) in TFA (5 mL) and DCM (15 mL) was stirred at room temperature overnight. The mixture was concentrated, neutralized with saturated aqueous Na₂CO₃, and extracted with DCM (50 mL). The organic layer was washed with water (30 mL×3), dried over Na₂SO₄, and concentrated to give the crude product (530 mg, yield: 66%), which was used in the next step without further purification.

5. Preparation of 2-fluoro-5-methoxy-N-(4-(4-oxo-1,3,4,5-tetra-hydro-[1,4]oxazepino[5,6,7-cd]indazol-8-yl)phenyl)benzenesulfonamide To a mixture of 2-((3-amino-6-(4-(2-fluoro-5-methoxy-phenylsulfon-amido)phenyl)-1H-indazol-4-yl)oxy)acetic acid (330 mg, 0.678 mmol), HATU (387 mg, 1 mmol) in DMF (50 mL) was added DIPEA (262 mg, 2.0 mmol). The mixture was stirred at RT, diluted with EtOAc (100 mL), filtered through celite, concentrated and purified by prep-TLC to give the title compound (110 mg, yield: 34%). MS-ESI: 469.2 (M+1)⁺, ¹H NMR (400 MHz, DMSO) δ 12.57 (s, 1H), 11.22 (s, 1H), 10.77 (s, 1H), 7.59 (d, J=8.7 Hz, 2H), 7.35 (t, J=9.4 Hz, 1H), 7.28 (dd, J=5.5, 3.2 Hz, 1H), 7.26-7.13 (m, 4H), 6.75 (d, J=0.7 Hz, 1H), 4.75 (s, 2H), 3.76 (s, 3H).

IX. Preparation of N-(6-(3-amino-4-methoxy-1H-indazol-6-yl)pyridin-3-yl)-2-fluoro-5-methoxybenzenesulfonamide (I)

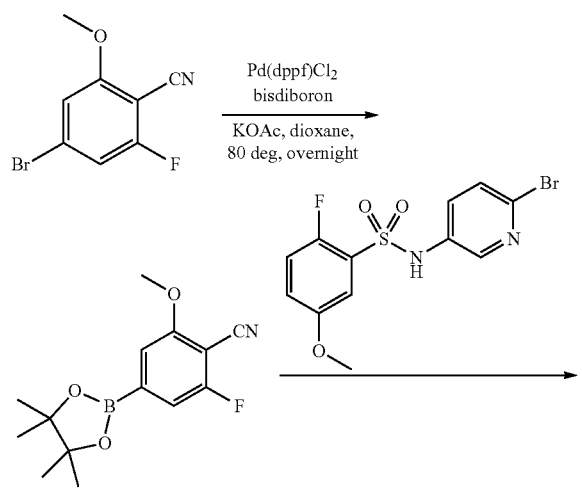

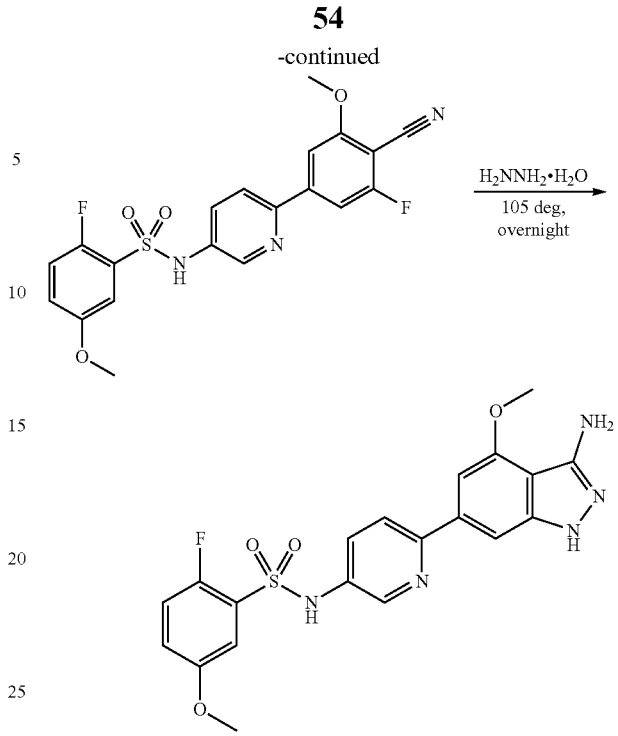

1. Preparation of N-(6-(4-cyano-3-fluoro-5-methoxyphenyl)-pyridin-3-yl)-2-fluoro-5-methoxybenzenesulfonamide A mixture of 4-bromo-2-fluoro-6-methoxybenzonitrile (300 mg, 1.3 mmol), bisdiboron (331 mg, 1.3 mmol), potassium acetate (510 mg, 5.2 mmol) Pd(dppf)Cl₂.DCM (106 mg, 0.13 mmol) in dioxane (10 mL) was heated under N₂ at 80° C. for overnight. To the reaction mixture was added N-(6-bromopyridin-3-yl)-2-fluoro-5-methoxybenzenesulfonamide (234 mg, 0.65 mmol), Cs₂CO₃ (348 mg, 1.06 mmol) and H₂O (2 mL). The mixture was heated under N₂ at 100° C. overnight. The mixture was cooled to room temperature, diluted with EtOAc (30 mL), filtered through celite, concentrated and purified by silica gel chromatography eluting with ethyl acetate in hexane (10-50 percent) to afford the title compound (160 mg, yield: 57%).

2. Preparation of N-(6-(3-amino-4-methoxy-1H-indazol-6-yl)pyridin-3-yl)-2-fluoro-5-methoxybenzenesulfonamide To a solution of N-(6-(4-cyano-3-fluoro-5-methoxyphenyl)pyridin-3-yl)-2-fluoro-5-methoxybenzenesulfonamide (140 mg, 0.324 mmol) in n-butanol (3 mL) was added 85% hydrazine hydrate (114 mg, 6 eq.). The mixture was heated to 105° C. in a capped vial for 16 h. The reaction mixture was cooled to rt, diluted with EtOAc (30 mL), washed with water (5 mL), dried over Na₂SO₄ and concentrated. The residue was purified by prep-TLC to give the title compound (46 mg, yield: 32%). MS-ESI: 444.2 (M+1)⁺, ¹H NMR (400 MHz, DMSO) δ 11.52 (s, 1H), 10.96 (s, 1H), 8.39 (d, J=2.4 Hz, 1H), 7.91 (d, J=8.7 Hz, 1H), 7.57 (dd, J=8.7, 2.6 Hz, 1H), 7.42-7.33 (m, 2H), 7.33-7.19 (m, 2H), 6.94 (s, 1H), 4.99 (s, 2H), 3.97-3.86 (m, 3H), 3.74 (d, J=17.4 Hz, 3H).

X. Preparation of N-(4-(3-amino-1H-pyrazolo[3,4-b]pyridin-6-yl)-phenyl)-2-fluoro-5-methoxybenzenesulfonamide (J)

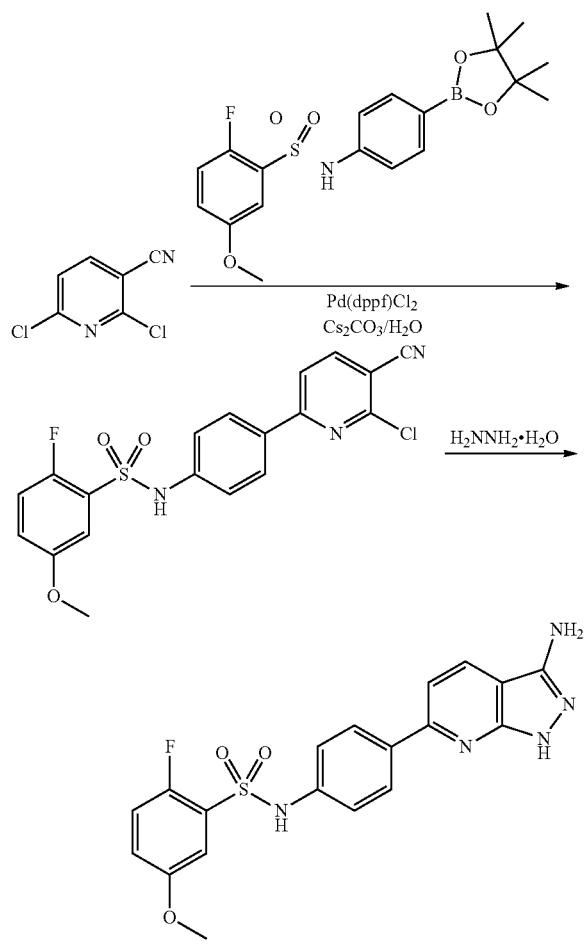

1. Preparation of N-(4-(6-chloro-5-cyanopyridin-2-yl)phenyl)-2-fluoro-5-methoxybenzenesulfonamide A mixture of 2,6-dichloronicotinonitrile (100 mg, 0.57 mmol), 2-fluoro-5-methoxy-N-(4-(4,4,5,5-tetramethyl-1,3,2-dioxaborolan-2-yl)phenyl)benzenesulfonamide (259 mg, 0.63 mmol), Pd(dppf)Cl$_2$.DCM (47 mg, 0.057 mmol) and Cs$_2$CO$_3$ (376 mg, 1.15 mmol) in dioxane (5 mL) and H$_2$O (0.8 mL) was heated under N$_2$ at 100° C. for 16 h. The mixture was cooled to room temperature, diluted with EtOAc (30 mL), filtered through celite, concentrated and purified by silica gel chromatography eluting with ethyl acetate in hexane (10-50 percent) to afford the title compound (168 mg, yield: 69%).

2. Preparation of N-(4-(3-amino-1H-pyrazolo[3,4-b]pyridin-6-yl)phenyl)-2-fluoro-5-methoxybenzenesulfonamide To a solution of N-(4-(6-chloro-5-cyanopyridin-2-yl)phenyl)-2-fluoro-5-methoxybenzenesulfonamide (168 mg, 0.4 mmol) in n-butanol (3 mL) was added 85% hydrazine hydrate (120 mg, 6 eq.). The mixture was heated to 130° C. in a capped vial for 16 h. The reaction mixture was cooled to rt, diluted with EtOAc (30 mL), washed with water (5 mL), dried over Na$_2$SO$_4$ and concentrated. The residue was purified by prep-TLC to give the title compound (60 mg, yield: 36%). MS-ESI: 414.2 (M+1)$^+$, $^1$H NMR (400 MHz, DMSO) δ 11.88 (s, 1H), 8.10 (d, J=8.4 Hz, 1H), 7.96 (d, J=8.7 Hz, 2H), 7.43 (d, J=8.3 Hz, 1H), 7.31 (m, 2H), 7.19 (t, J=8.6 Hz, 3H), 5.53 (s, 2H), 3.75 (s, 3H).

XI. Preparation of N-(4-(3-amino-1H-indazol-6-yl)phenyl)-2-fluoro-5-methoxybenzenesulfonamide (K)

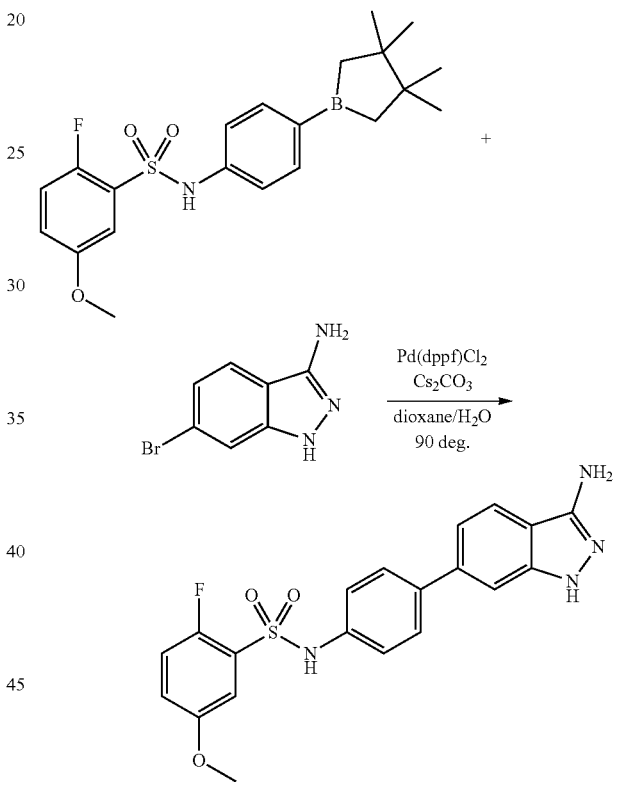

A mixture of 6-bromo-1H-indazol-3-amine (50 mg, 0.236 mmol), 2-fluoro-5-methoxy-N-(4-(4,4,5,5-tetramethyl-1,3,2-dioxaborolan-2-yl)phenyl)benzenesulfonamide (106 mg, 0.259 mmol), Pd(dppf)Cl$_2$.DCM (10 mg, 0.012 mmol) and Cs$_2$CO$_3$ (154 mg, 0.472 mmol) in dioxane (3 mL) and H$_2$O (0.3 mL) was heated under N$_2$ at 90° C. for 18 h. The mixture was cooled to room temperature, diluted with EtOAc (30 mL), filtered through celite, concentrated and purified by silica gel chromatography eluting with DCM:MeOH (100:1 to 50:1) to afford the title compound (77 mg, yield: 79%). ESI-MS: 413.2 (M+1)$^+$, $^1$H NMR (400 MHz, DMSO) δ 11.41 (s, 1H), 10.75 (s, 1H), 7.69 (d, J=8.4 Hz, 1H), 7.58 (d, J=8.5 Hz, 2H), 7.39-7.26 (m, 3H), 7.25-7.17 (m, 3H), 7.11 (d, J=8.5 Hz, 1H), 5.35 (s, 2H), 3.76 (s, 3H).

XI. Preparation of N-(4-(3-amino-1H-pyrazolo[3,4-b]pyridin-6-yl)-phenyl)-2-chloro-5-methoxybenzenesulfonamide (L)

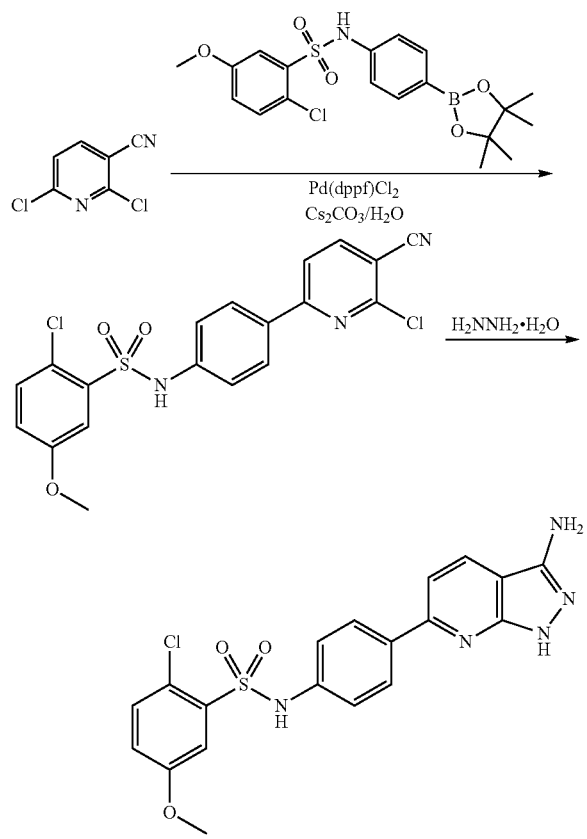

1. Preparation of 2-chloro-N-(4-(6-chloro-5-cyanopyridin-2-yl)-phenyl)-5-methoxybenzenesulfonamide A mixture of 4-bromo-2-fluoro-6-methylbenzonitrile (60 mg, 0.34 mmol), 2-chloro-5-methoxy-N-(4-(4,4,5,5-tetramethyl-1,3,2-dioxaborolan-2-yl)phenyl)benzenesulfonamide (161 mg, 0.38 mmol), Pd(dppf)Cl$_2$.DCM (28 mg, 0.03 mmol) and Cs$_2$CO$_3$ (225 mg, 0.69 mmol) in dioxane (4 mL) and H$_2$O (0.5 mL) was heated under N$_2$ at 100° C. for 3 h. The mixture was cooled to room temperature, diluted with EtOAc (30 mL), filtered through celite, concentrated and purified by silica gel chromatography eluting with ethyl acetate in hexane (10-50 percent) to afford the title compound (70 mg, yield: 46%).

2. Preparation of N-(4-(3-amino-1H-pyrazolo[3,4-b]pyridin-6-yl)-phenyl)-2-chloro-5-methoxybenzenesulfonamide To a solution of 2-chloro-N-(4-(6-chloro-5-cyanopyridin-2-yl)phenyl)-5-methoxybenzenesulfonamide (70 mg, 0.16 mmol) in n-butanol (2 mL) was added 85% hydrazine hydrate (48 mg). The reaction mixture was heated to 130° C. in a capped vial for 18 h. The reaction mixture was cooled to room temperature and concentrated. The residue was concentrated and purified by pre-TLC (DCM:MeOH=12:1) to give the title compound (50 mg, yield: 72%). MS-ESI: 430.2 (M+1)$^+$, 1H NMR (400 MHz, DMSO) δ 11.86 (s, 1H), 8.09 (d, J=8.4 Hz, 1H), 7.94 (d, J=8.5 Hz, 2H), 7.56-7.38 (m, 4H), 7.22-7.09 (m, 3H), 5.51 (s, 2H), 3.78 (s, 3H).

XIII. Preparation of N-(4-(3-amino-1H-pyrazolo[4,3-c]pyridin-6-yl)phenyl)-2-fluoro-5-methoxybenzenesulfonamide (M)

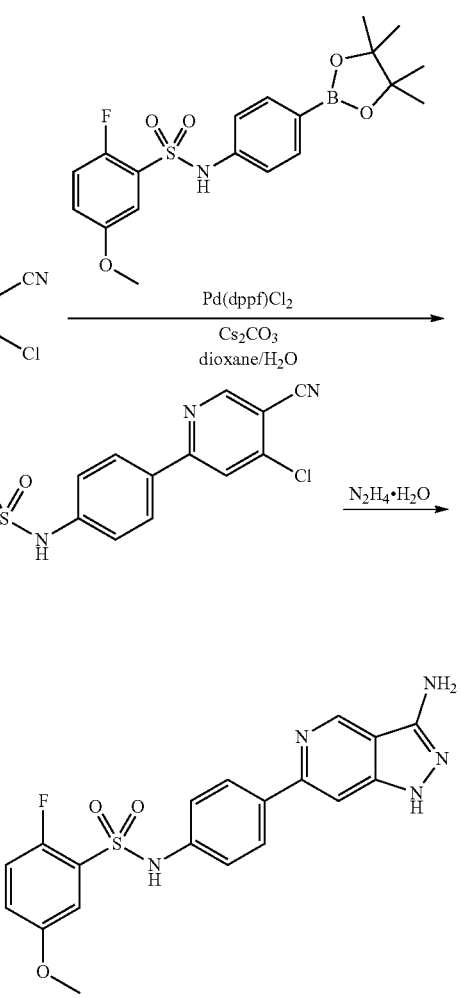

1. Preparation of N-(4-(4-chloro-5-cyanopyridin-2-yl)phenyl)-2-fluoro-5-methoxybenzenesulfonamide A mixture of 4,6-dichloronicotinonitrile (100 mg, 0.58 mmol), 2-fluoro-5-methoxy-N-(4-(4,4,5,5-tetramethyl-1,3,2-dioxaborolan-2-yl)phenyl)benzenesulfonamide (259 mg, 0.636 mmol), Pd(dppf)Cl$_2$.DCM (24 mg, 0.024 mmol) and Cs$_2$CO$_3$ (381 mg, 1.16 mmol) in dioxane (3 mL) and H$_2$O (0.5 mL) was heated under N$_2$ at 100° C. for 6 h. The mixture was cooled to room temperature, diluted with EtOAc (30 mL), filtered through celite, concentrated and purified by silica gel chromatography eluting with ethyl acetate in hexane (0-30 percent) to afford the title compound (244 mg, yield: 100%).

2. Preparation of N-(4-(3-amino-1H-pyrazolo[4,3-c]pyridin-6-yl)-phenyl)-2-fluoro-5-methoxybenzenesulfonamide To a solution of N-(4-(4-chloro-5-cyanopyridin-2-yl)phenyl)-2-fluoro-5-methoxybenzenesulfonamide (100 mg, 0.239 mmol) in iPrOH (15 mL) was added 85% hydrazine hydrate (72 mg, 1.435 mmol). The mixture was heated to 85° C. in a capped vial for 4 h. The reaction mixture was cooled to room temperature and concentrated. The residue was concentrated and purified by pre-TLC (DCM:MeOH=10:1) to give the title compound (20 mg, yield: 20%). MS-ESI: 413.2 (M+1)+, $^1$H NMR (400 MHz, DMSO) δ 10.89 (s, 1H), 8.39 (m, 1H), 8.03-7.78 (m, 2H), 7.44-7.06 (m, 5H), 4.51 (s, 2H), 3.74 (s, 3H).

XIV. Preparation of N-(6-(3-amino-1H-indazol-6-yl)pyridin-3-yl)-2-fluoro-5-methoxybenzenesulfonamide (N)

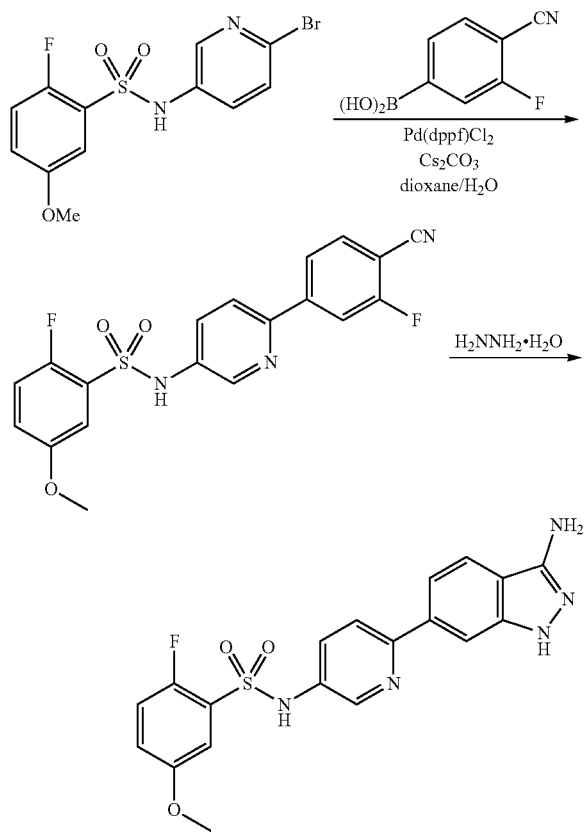

1. Preparation of N-(6-(4-cyano-3-fluorophenyl)pyridin-3-yl)-2-fluoro-5-methoxybenzenesulfonamide A mixture of N-(6-bromopyridin-3-yl)-2-fluoro-5-methoxybenzene-sulfonamide (300 mg, 0.83 mmol), (4-cyano-3-fluorophenyl)boronic acid (137 mg, 0.83 mmol), Pd(dppf)Cl$_2$·DCM (68 mg, 0.083 mmol) and Cs$_2$CO$_3$ (541 mg, 1.66 mmol) in dioxane (5 mL) and H$_2$O (0.8 mL) was heated under N$_2$ at 100° C. for 16 h. The mixture was cooled to room temperature, diluted with EtOAc (30 mL), filtered through celite, concentrated and purified by silica gel chromatography eluting with ethyl acetate in hexane (10-50 percent) to afford the title compound (150 mg, yield: 45%).

2. Preparation of N-(6-(3-amino-1H-indazol-6-yl)pyridin-3-yl)-2-fluoro-5-methoxybenzenesulfonamide To a solution of N-(6-(4-cyano-3-fluorophenyl)pyridin-3-yl)-2-fluoro-5-methoxybenzenesulfonamide (150 mg, 0.373 mmol) in n-butanol (3 mL) was added 85% hydrazine hydrate (132 mg, 6 eq.). The mixture was heated to 120° C. in a capped vial for 16 h. The reaction mixture was cooled to rt, diluted with EtOAc (30 mL), washed with water (5 mL), dried over Na$_2$SO$_4$ and concentrated. The residue was purified by prep-TLC to give the title compound (30 mg, yield: 19%). MS-ESI: 414.3 (M+1)+, $^1$H NMR (400 MHz, DMSO) δ 11.48 (s, 1H), 10.96 (s, 1H), 8.40 (d, J=2.5 Hz, 1H), 7.90 (d, J=8.7 Hz, 1H), 7.81 (s, 1H), 7.70 (d, J=8.5 Hz, 1H), 7.58 (dd, J=8.7, 2.6 Hz, 1H), 7.51 (dd, J=8.5, 1.1 Hz, 1H), 7.37 (t, J=9.4 Hz, 1H), 7.29 (dd, J=5.5, 3.2 Hz, 1H), 7.22 (m, 1H), 5.35 (s, 2H), 3.76 (s, 3H).

XV. Preparation of N-(2-(3-amino-1H-indazol-6-yl)pyrimidin-5-yl)-2-fluoro-5-methoxybenzenesulfonamide (O)

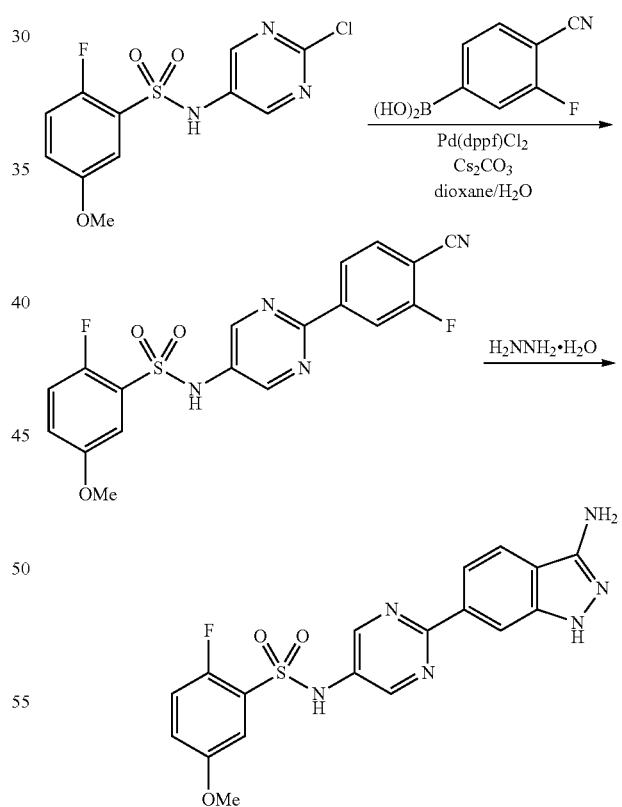

1. Preparation of N-(2-(4-cyano-3-fluorophenyl)pyrimidin-5-yl)-2-fluoro-5-methoxybenzenesulfonamide A mixture of N-(2-chloropyrimidin-5-yl)-2-fluoro-5-methoxybenze-nesulfonamide (200 mg, 0.63 mmol), (4-cyano-3-fluorophenyl)boronic acid (104 mg, 0.63 mmol), Pd$_2$dba$_3$ (57 mg, 0.063 mmol) and Cs$_2$CO$_3$ (410 mg, 1.26 mmol) in dioxane (5 mL) and H$_2$O (0.8 mL) was heated under N$_2$ at 110° C. for 16 h. The mixture was cooled to room temperature, diluted with EtOAc (30 mL), filtered through celite, concentrated and purified by silica gel chromatography eluting with ethyl acetate in hexane (10-50 percent) to afford the title compound (125 mg, yield: 49%).

2. Preparation of N-(2-(3-amino-1H-indazol-6-yl)pyrimidin-5-yl)-2-fluoro-5-methoxybenzenesulfonamide To a solution of N-(2-(4-cyano-3-fluorophenyl)pyrimidin-5-yl)-2-fluoro-5-methoxybenzenesulfonamide (125 mg, 0.31 mmol) in n-butanol (3 mL) was added 98% hydrazine hydrate (40 mg, 4 eq.). The mixture was heated to 135° C. in a capped vial for 16 h. The reaction mixture was cooled to rt, diluted with EtOAc (30 mL), washed with water (5 mL), dried over Na$_2$SO$_4$ and concentrated. The residue was purified by prep-TLC to give the title compound (10 mg, yield: 7%). MS-ESI: 414.2 (M+1)$^+$, $^1$H NMR (400 MHz, DMSO) δ 11.61 (s, 1H), 8.69-8.62 (m, 2H), 8.18 (s, 1H), 7.86 (dd, J=8.5, 1.3 Hz, 1H), 7.75 (d, J=8.4 Hz, 1H), 7.40 (t, J=9.4 Hz, 1H), 7.34 (dd, J=5.5, 3.2 Hz, 1H), 7.27 (dt, J=9.0, 3.6 Hz, 1H), 5.35 (dd, J=23.3, 18.5 Hz, 2H), 3.80 (s, 3H).

Exemplary Assay Protocols:

1. Enzyme Based Assays for SGK1, SGK2, SGK3, and Akt1

The kinase enzymatic reaction is carried out with a biotinylated Akt Substrates-2 peptide substrate. The phosphorylated substrate is then detected using a specific anti-phospho peptide antibody which is coupled with Eu$^{3+}$ Cryptate and XL665 conjugated with streptavidin.

Exemplary Assay Conditions

Enzyme: ~0.1 nM
Substrate: 0.2 μM
ATP: 50 μM and 1 mM
Mg$^{2+}$: 10 mM
Reaction time: 60 min with 50 μM ATP and 30 min with 1 mM ATP
SA-XL to Biotin: 1:10

Detailed Steps 1. prepare the enzyme and substrate solution with the buffer from Cisbio
2. add the enzyme and substrate solution to the diluted compound plate
3. transfer 5 μL of compound, enzyme, and substrate mixture to an 384-well assay plate
4. add 5 μL ATP (with Mg$^{2+}$) solution to initiate the reaction
5. after certain time, add 10 μL of stop solution containing SA-XL and specific antibody
6. read the plate after 2 h incubation at rt
7. process the data using prizm software (Exemplary results are shown in FIG. 1.)

2. PK Studies Protocol

3 Male mice/group, 8 groups total with Intravenous and Oral Administration, then measure the compound concentration in plasma.

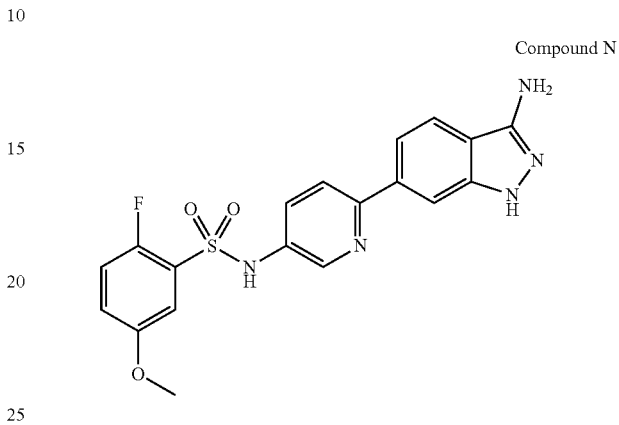

Compound N

An example is shown in FIG. 2, which shows a concentration-time curve of Compound N in male ICR mice following intravenous and oral administration.

Selected Pharmacokinetics Parameters of Compound N in Male ICR Mice Following Intravenous and Oral Administration

|  | AUC$_{(0-t)}$ μg/L*hr | AUC$_{(0-∞)}$ μg/L*hr | MRT$_{(0-∞)}$ hr | t$_{1/2z}$ hr | T$_{max}$ Hr | Vz L/kg | CLz L/hr/kg | C$_{max}$ μg/L | F* % |
|---|---|---|---|---|---|---|---|---|---|
| IV (2 mg/kg) | 151052.68 | 165159.99 | 8.84 | 6.99 | 0.08 | 0.12 | 0.01 | 29080.03 |  |
| PO (20 mg/kg) | 957290.48 | 1530870.55 | 24.12 | 17.27 | 0.25 | NA | NA | 71907.48 | 63.37 |

*F is calculated from AUC$_{(0-t)}$.

3. Kinase Profiling Protocol

Figure 3:
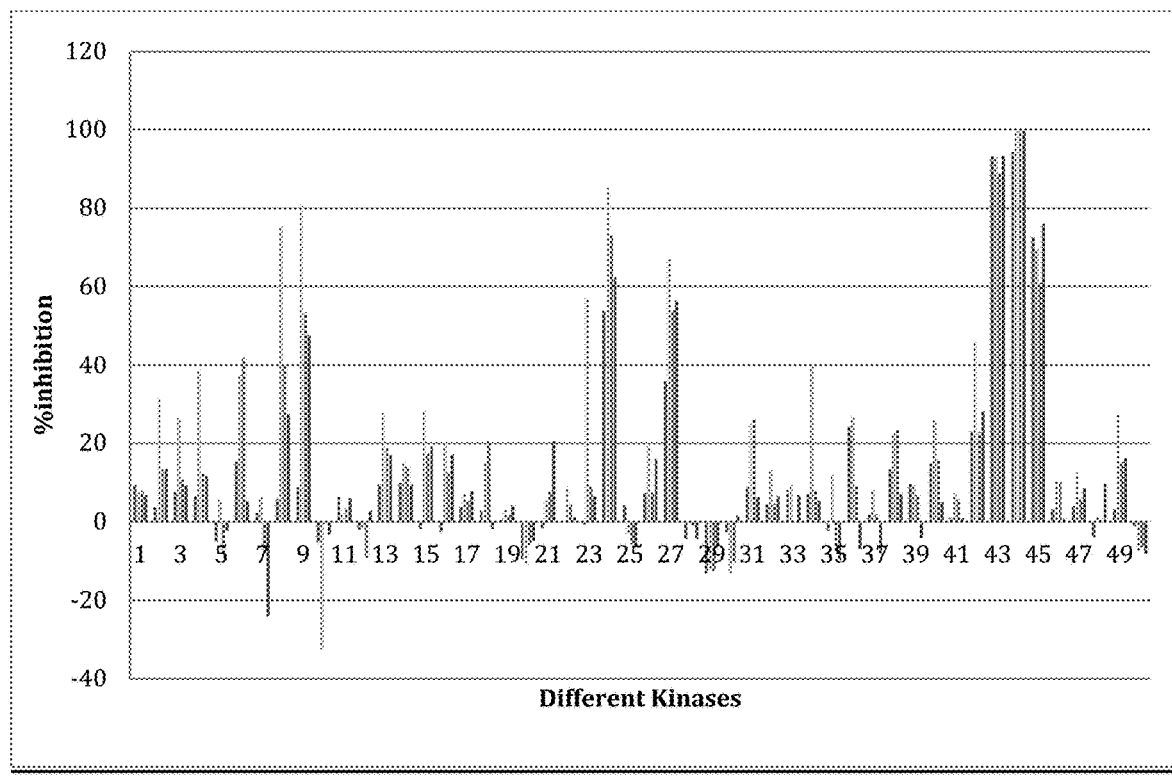
FIG. 3 schematically shows 50 kinase profiling data, all kinase selected are human kinases with their specific substrates.

Kinase profiling is performed against 50 kinase targets at 1 concentration (1 μM) in duplicates using radiometric assay. All kinase selected are human kinases with their specific substrates. The results are observed as % activity change compared to control. An exemplary data showing kinase profiling provided in FIG. 3.

4. hERG Assay Protocol:

Assay platform & method: Automated patch clamp (Qpatch-48)
Cell source: CHO cell line stably expressing hERG channels
Measured parameter: Whole-cell tail current of hERG channels
Test concentration: 6 concentrations (30, 10, 3, 1, 0.3, 0.1 μM)

Example: Qpatch hERG Assay

| Compound | Qpatch hERG IC50 (μM) | Comments |
|---|---|---|
| J | >30 | Highest test concentration: 30 μM |
| C | >30 | Highest test concentration: 30 μM |

| Compound | Qpatch hERG IC50 (µM) | Comments |
|---|---|---|
| E | >30 | Highest test concentration: 30 µM |
| D | 12.22 | Fitting curve Hillslope = 0.88 |

Figure 4:
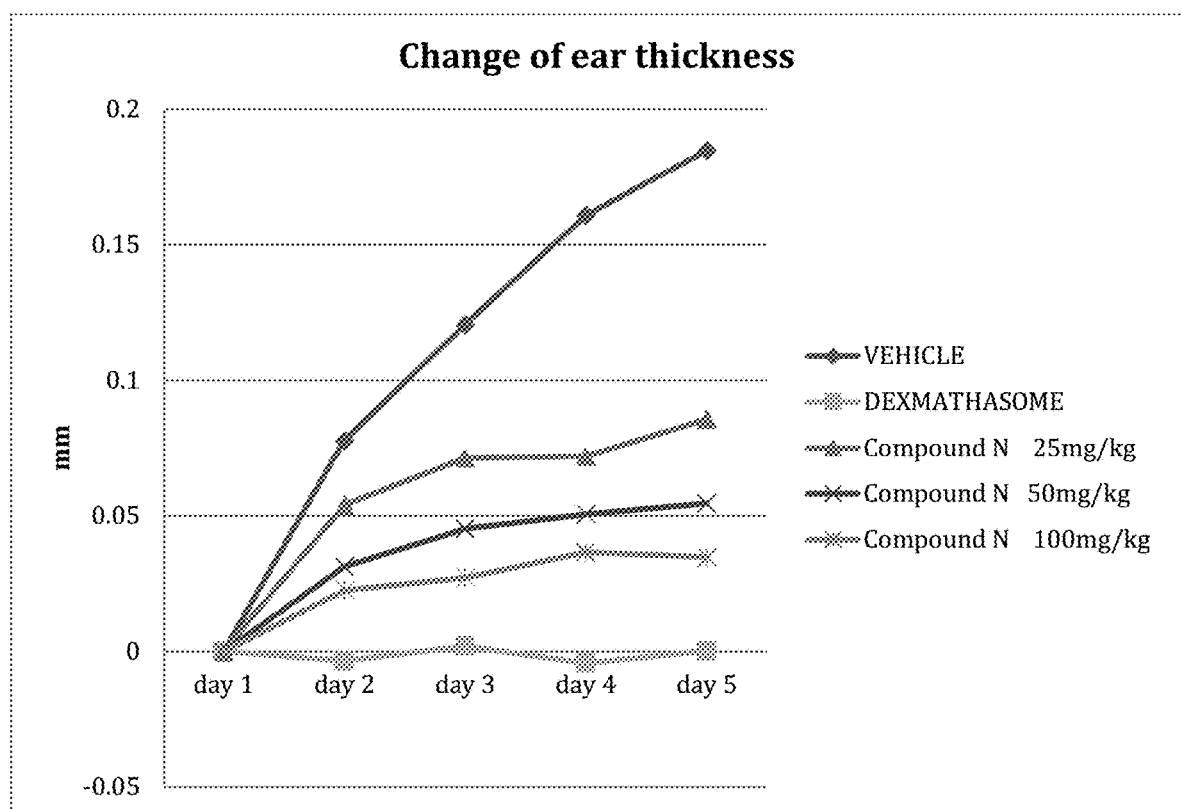
FIG. 4 schematically shows the change of ear thickness of compound N with different concentrations.
Figure 5:
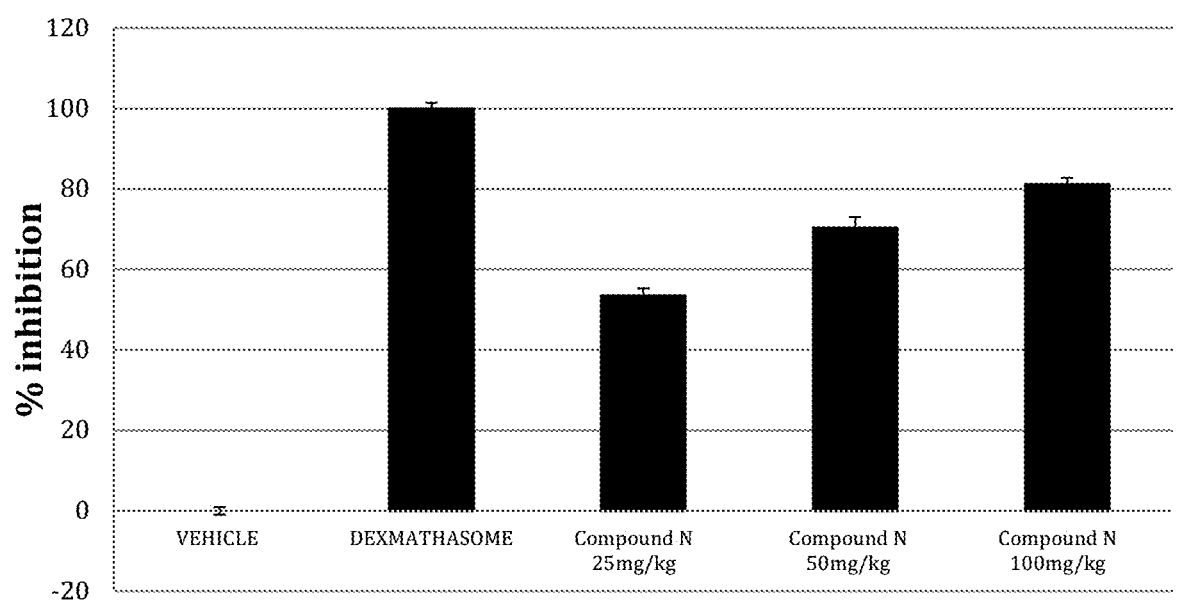
FIG. 5 schematically shows data on % inhibition in ear thickness (compound N) after daily IL-23 injection.

5. Exemplary IL-23 Animal Model Protocol:
Animal: 15 BALB/C Female mice from CRL (9 wks)
Model: IL-23 from Biolegend, qd×4 at 0.4 mcg/ear, both sides of ears, starting on Day 1
Treatment: 5 groups and 3 per group
  1) Vehicle: 0.5% CMCNa
  2) Dexamethasone: 2 mg/kg, ip qd×4, 5% DMSO in saline
  3) Compound N: 25 mg/kg, po, bid×4, 0.5% CMC-Na
  4) Compound N: 50 mg/kg, po, bid×4, 0.5% CMC-Na
  5) Compound N: 100 mg/kg, po, bid×4, 0.5% CMC-Na
Marker: body weight, and ear thickness (prior to IL-23 administration and ever the other day) during study.
Spleen weight and IL-17 levels in ear homogenates with protease PBS at the end
Exemplary data (Compound N) showing change of ear thickness is provided in FIG. 4. FIG. 5 shows data on % Inhibition In Ear Thickness (Compound N) After Daily IL-23 injection.

Figure 6:
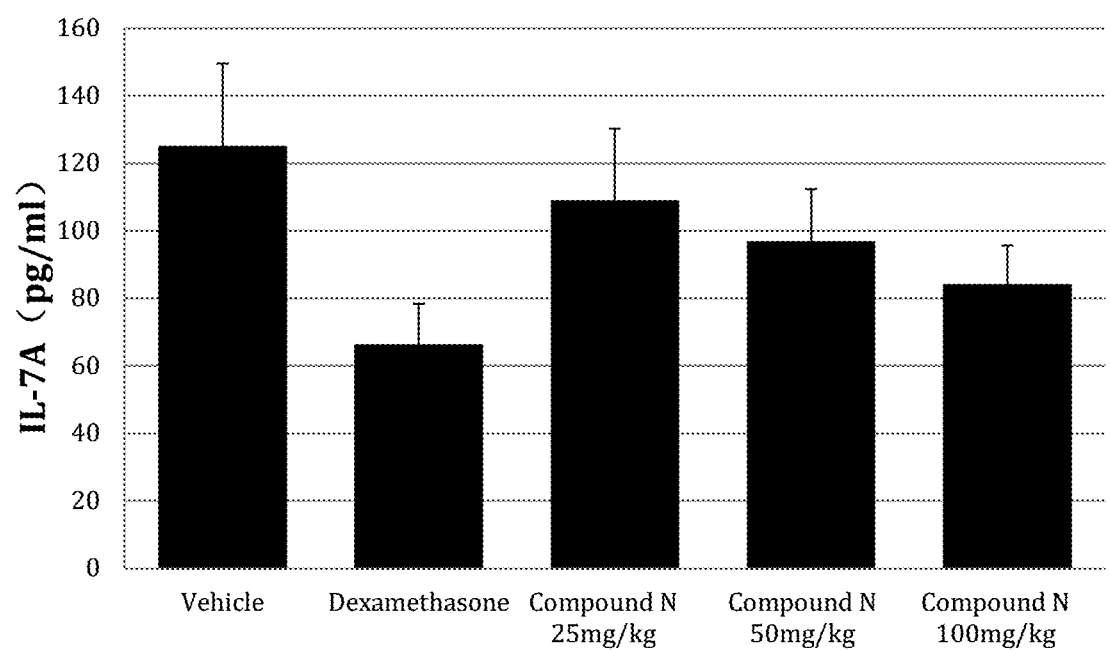
FIG. 6 schematically shows data (compound N) on IL-17A measured in ear samples by ELISA assay.

6. Exemplary IL-17A ELISA Assay Protocol:
Use the Mouse IL-17A ELISA Max™ Deluxe assay kit from BioLegend.
  Sample: Mouse ear homogenates in protease buffer
  Positive control: Mouse IL-17A standard
  Example: Compound N
Exemplary data (Compound N) on IL-17A measured in ear samples by ELISA assay is shown in FIG. 6.

Figure 7:
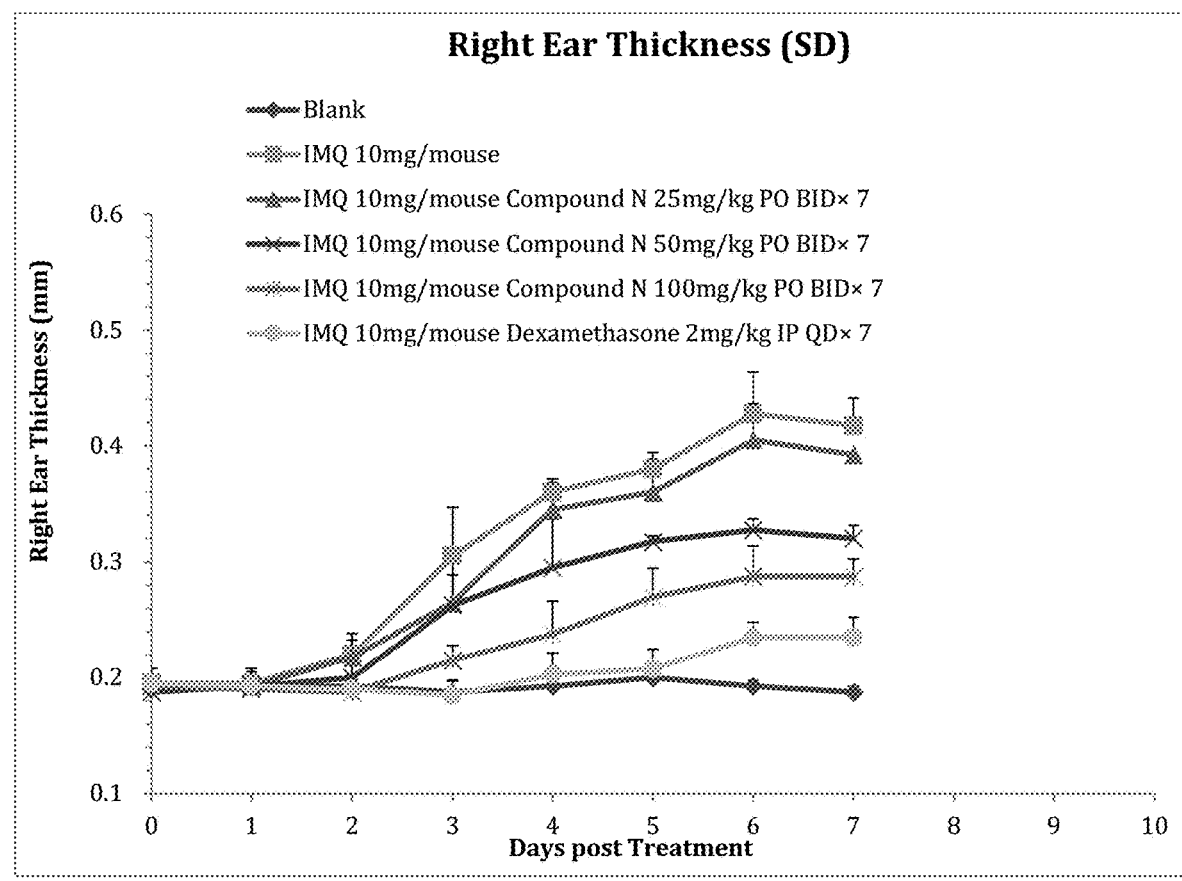
FIG. 7 schematically shows the change of right ear thickness of compound N with different concentrations.

7. Imiquimod-Induced Psoriasis-Like Skin Inflammation Protocol
Animal: BALB/C Female mice from BK. Ltd. Shanghai, China (8 wks)
Model: The psoriasis-like skin inflammation mouse model will be generated by daily topical application of a dose of 10 mg/cm$^2$ IMQ cream (5%) on the inside of the right ear for 7 consecutive days.
Treatment: 6 groups and 6 per group
  1) 20 mg/cm2 IMQ cream (5%), Vehicle: bid×7, 0.5% CMCNa
  2) 20 mg/cm2 IMQ cream (5%), Dexamethasone: 2 mg/kg, ip qd×7, 5% DMSO in saline
  3) 20 mg/cm2 IMQ cream (5%), Compound N: 25 mg/kg, po, bid×7, 0.5% CMC-Na
  4) 20 mg/cm2 IMQ cream (5%), Compound N: 50 mg/kg, po, bid×7, 0.5% CMC-Na
  5) 20 mg/cm2 IMQ cream (5%), Compound N: 100 mg/kg, po, bid×7, 0.5% CMC-Na
  6) Blank (untreated)
Marker: body weight, and ear thickness during study.
Exemplary data is shown in FIG. 7.

Figure 8:
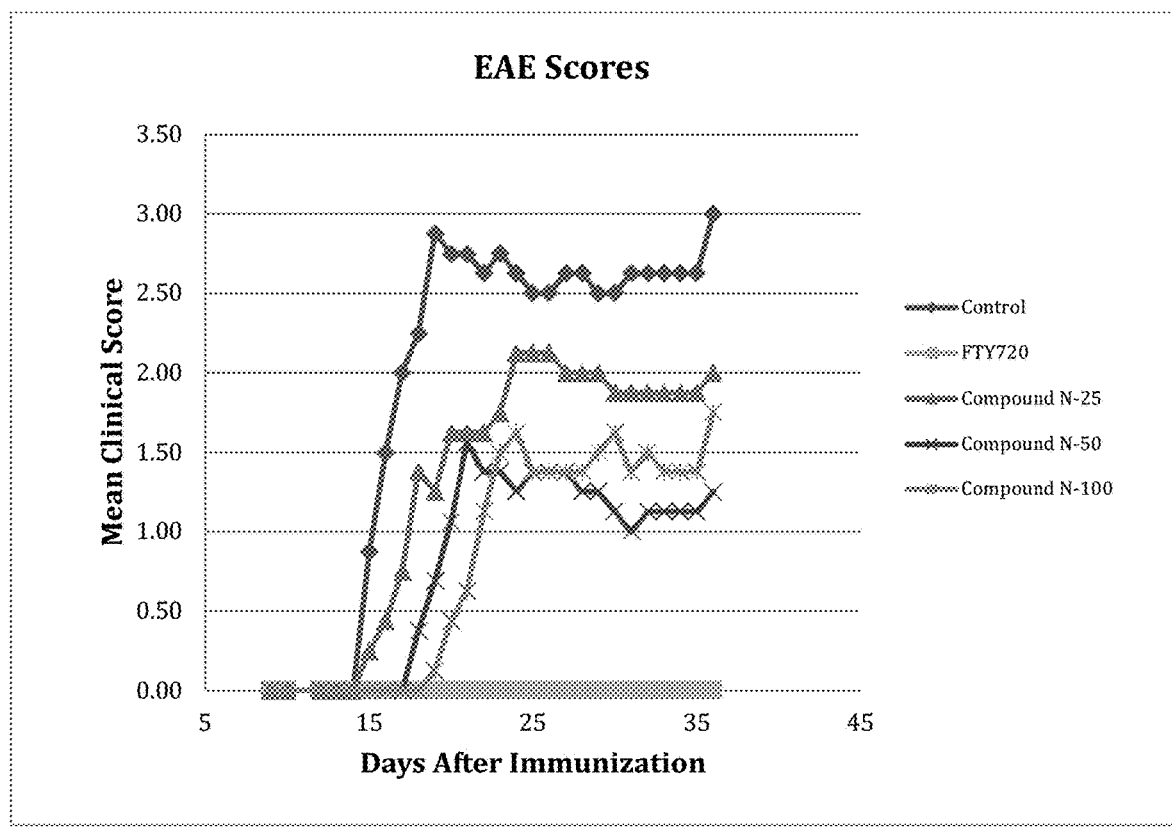
FIG. 8 schematically shows EAE scores of compound N with different concentrations.

8. EAE Animal Model Protocol:
Animal: 40 C57BL/6 female 10 weeks old, mice from CRL
Mice will be administered antigen (MOG35-55/CFA) emulsion s.c. at two sites, 0.1 mL/site (0.2 mL/mouse total head and tail), and inject of freshly prepared PTX solution i.p. (0.1 mL/dose) within 1 to 6 hours after. Next day, mice will be injected freshly prepared PTX solution i.p. again.
Mice will be assigned into 5 groups with 8 mice per group.
  G1: Vehicle 1% CMCNa
  G2: FTY720 3 mg/kg QD, po 5 mL/kg,
  G3: Compound N 25 mg/kg, BID, po 5 mL/kg, 1% CMCNa, 4 wks D0-D35
  G4: Compound N 50 mg/kg, BID, po 5 mL/kg, 1% CMCNa, 4 wks D0-D35
  G5: Compound N 100 mg/kg, BID, po 5 mL/kg, 1% CMCNa, 4 wks D0-D35
Starting Day 0 after immunization, disease severity will be scored daily on a 5 point scale and body weight will be monitored as well.
Exemplary data is shown in FIG. 8.

TABLE 2

Exemplary Testing Results

| Structure | Sgk2 (50 µM ATP) | Sgk2 (1 mM ATP) | Sgk1 (50 µM ATP) | Sgk1 (1 mM ATP) | Sgk3 | HeLa | 293T | 293T_O |
|---|---|---|---|---|---|---|---|---|
| 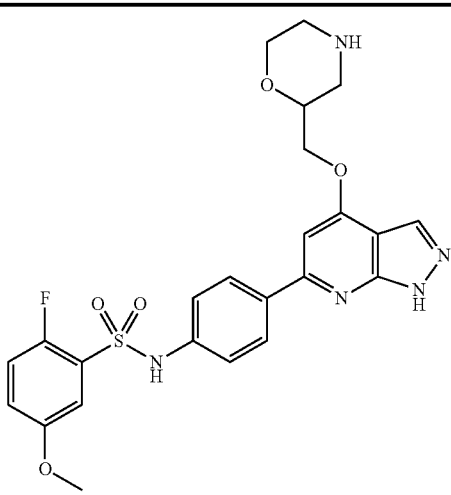 | 0.0035 | 0.0098 | 0.0034 | 0.0107 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 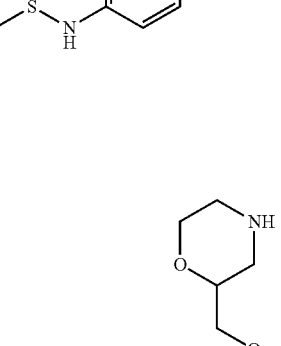 | 0.0008 | 0.0056 | 0.0031 | 0.0097 | | 35.8 | 47.89 | 61.18 |
| 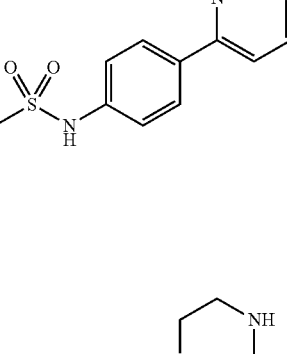 | 0.002 | 0.0158 | 0.0025 | 0.0069 | | 11.7 | 20.39 | 35.11 |
| 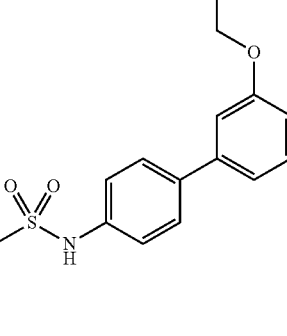 | 0.0018 | 0.0252 | 0.0018 | 0.0319 | | | | |

TABLE 2-continued

Exemplary Testing Results

| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 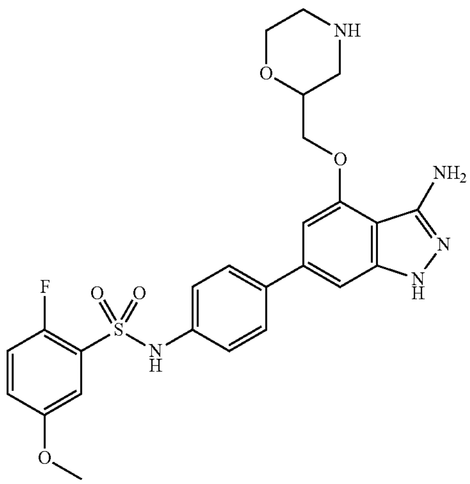 | 0.002 | 0.0038 | 0.0023 | 0.0039 | | | | |
| 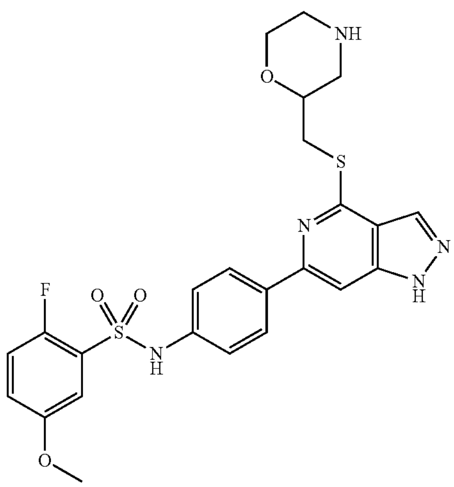 [SMILES: COc1ccc(F)c(S(=O)(=O)Nc2ccc(-c3cc4[nH]ncc4c(OCC4CNCCO4)n3)cc2)c1] | 0.0034 | 0.0041 | 0.0023 | 0.0066 | | 15.6 | 17.93 | 24.46 |
| 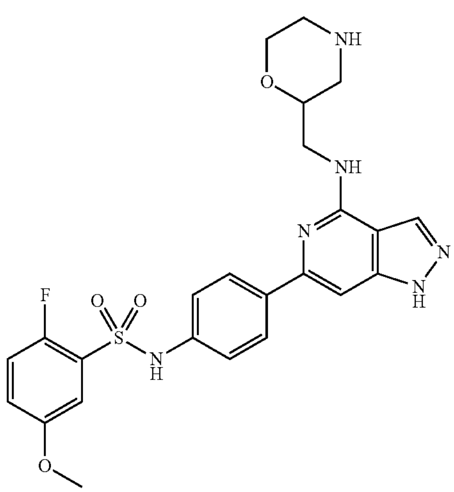 [SMILES: COc1ccc(F)c(S(=O)(=O)Nc2ccc(-c3cc4[nH]ncc4c(NCC4CNCCO4)n3)cc2)c1] | 0.0053 | 0.0035 | 0.0081 | 0.0042 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 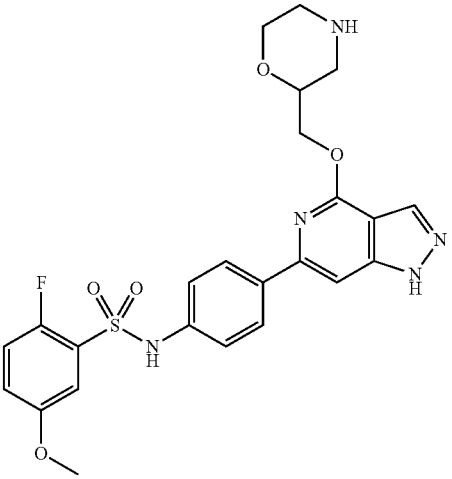 | 0.0016 | 0.01 | 0.0013 | 0.0134 | 0.1 | | | |
| 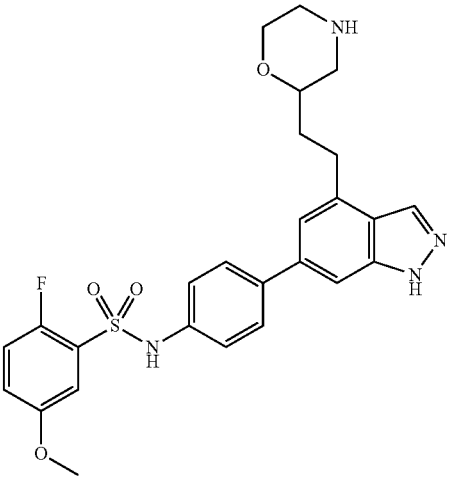 [SMILES: COc1ccc(F)c(S(=O)(=O)Nc2ccc(-c3cc(CCC4CNCCO4)c4cn[nH]c4c3)cc2)c1] | 0.0041 | 0.0082 | 0.0032 | 0.0116 | 0.15 | | | |
| 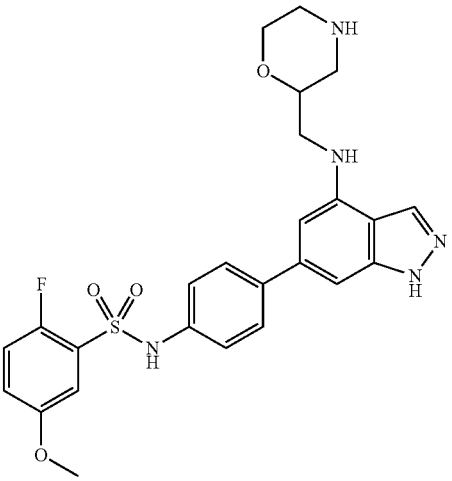 [SMILES: COc1ccc(F)c(S(=O)(=O)Nc2ccc(-c3cc(NCC4CNCCO4)c4cn[nH]c4c3)cc2)c1] | 0.0017 | 0.0066 | 0.0019 | 0.0124 | 0.15 | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 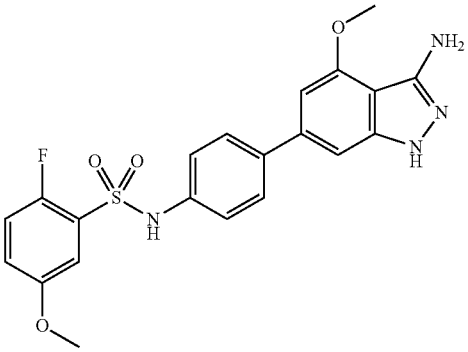 [SMILES: COc1ccc(F)c(S(=O)(=O)Nc2ccc(-c3cc(OC)c4c(N)n[nH]c4c3)cc2)c1] | 0.0051 | 0.0089 | 0.0024 | 0.0178 | 0.04 | | | |
| 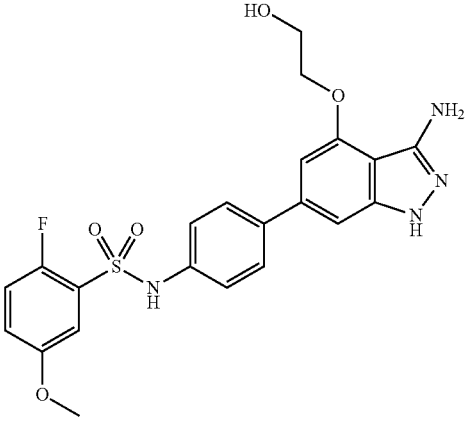 [SMILES: COc1ccc(F)c(S(=O)(=O)Nc2ccc(-c3cc(OCCO)c4c(N)n[nH]c4c3)cc2)c1] | 0.0079 | 0.0062 | 0.0051 | 0.0077 | 0.09 | | | |
| 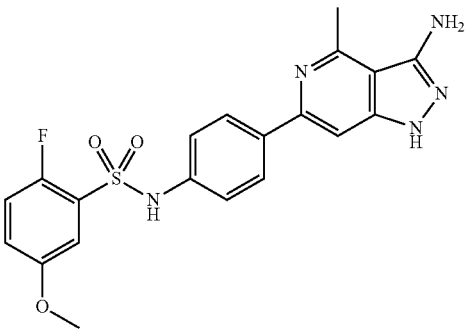 [SMILES: COc1ccc(F)c(S(=O)(=O)Nc2ccc(-c3cc4[nH]nc(N)c4c(C)n3)cc2)c1] | 0.0031 | 0.0053 | 0.0106 | 0.0085 | 0.05 | | | |
| 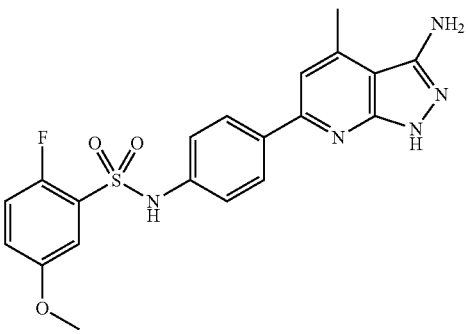 [SMILES: COc1ccc(F)c(S(=O)(=O)Nc2ccc(-c3cc(C)c4c(N)n[nH]c4n3)cc2)c1] | 0.0041 | 0.0037 | 0.0028 | 0.0055 | 0.03 | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 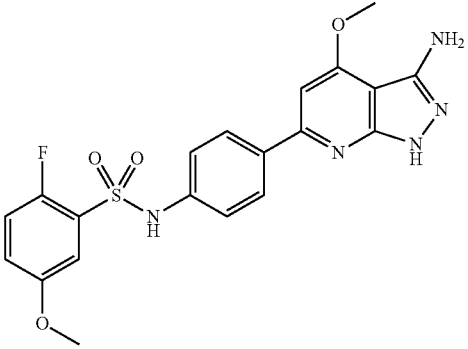 [SMILES: COc1ccc(F)c(S(=O)(=O)Nc2ccc(-c3cc(OC)c4c(N)n[nH]c4n3)cc2)c1] | 0.003 | 0.0357 | 0.0171 | 0.1121 | | | | |
| 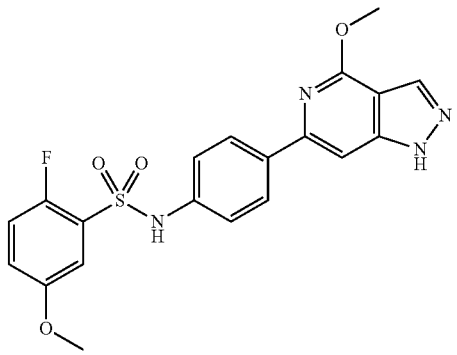 [SMILES: COc1ccc(F)c(S(=O)(=O)Nc2ccc(-c3cc4[nH]ncc4c(OC)n3)cc2)c1] | 0.0385 | 0.0327 | 0.0706 | | | | | |
| 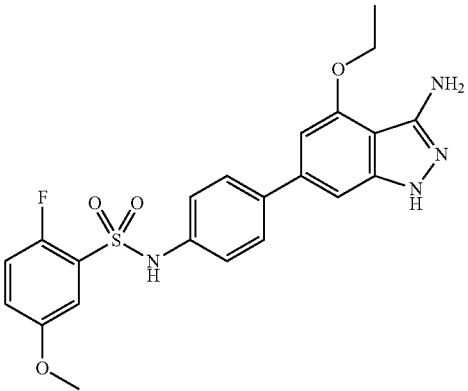 [SMILES: CCOc1cc(-c2ccc(NS(=O)(=O)c3cc(OC)ccc3F)cc2)cc2[nH]nc(N)c12] | 0.0123 | 0.0299 | 0.0118 | 0.002 | 0.13 | | | |

TABLE 2-continued

Exemplary Testing Results

| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| (structure) | 0.008 | 0.0213 | 0.0277 | 0.0928 | 0.1 | | | |
| (structure) | 0.0103 | 0.0164 | 0.0052 | 0.0029 | | | | |
| (structure) | 0.0046 | 0.0093 | 0.0055 | 0.0015 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 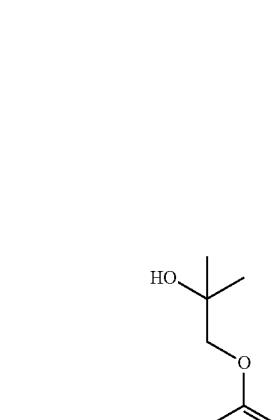 | 0.0044 | 0.0065 | 0.0086 | 0.0038 | | | | |
| 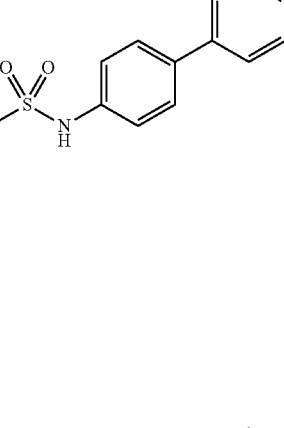 | 0.0383 | 0.0393 | 0.0361 | | | | | |
| 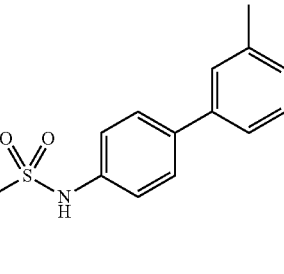 | 0.0084 | 0.0715 | 0.0215 | 0.0499 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 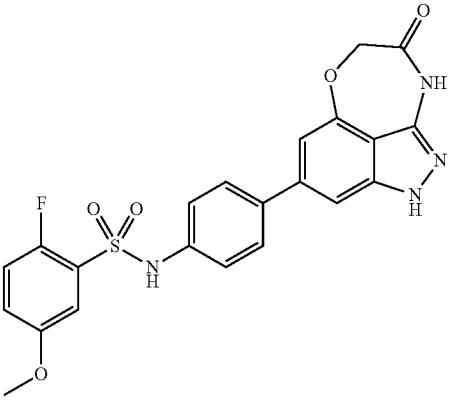 [SMILES: COc1ccc(F)c(S(=O)(=O)Nc2ccc(-c3cc4c5c(n[nH]c5c3)NC(=O)CO4)cc2)c1] | 0.0243 | 0.222 | 0.0306 | 0.9701 | | | | |
| 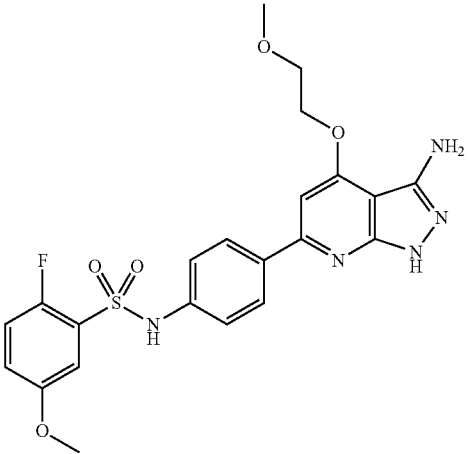 [SMILES: COCCOc1cc(-c2ccc(NS(=O)(=O)c3cc(OC)ccc3F)cc2)nc2[nH]nc(N)c12] | 0.0096 | 0.0694 | 0.0287 | 0.0104 | | | | |
| 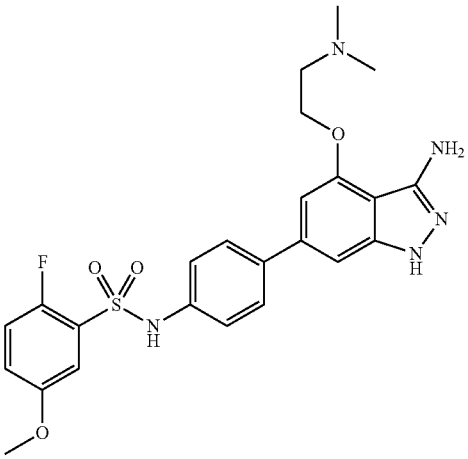 [SMILES: COc1ccc(F)c(S(=O)(=O)Nc2ccc(-c3cc(OCCN(C)C)c4c(N)n[nH]c4c3)cc2)c1] | 0.0091 | 0.1037 | 0.027 | 0.02 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 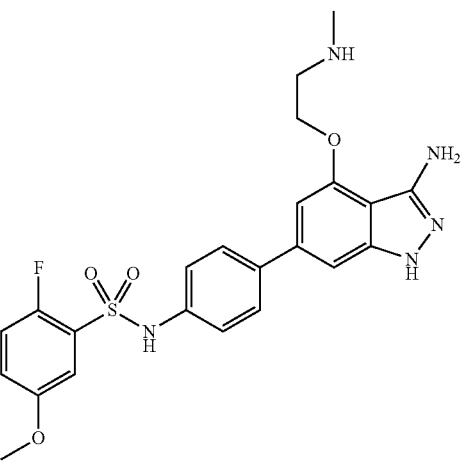 [SMILES: CNCCOc1cc(-c2ccc(NS(=O)(=O)c3cc(OC)ccc3F)cc2)cc2[nH]nc(N)c12] | 0.006 | 0.0388 | 0.0177 | 0.0113 | | | | |
| 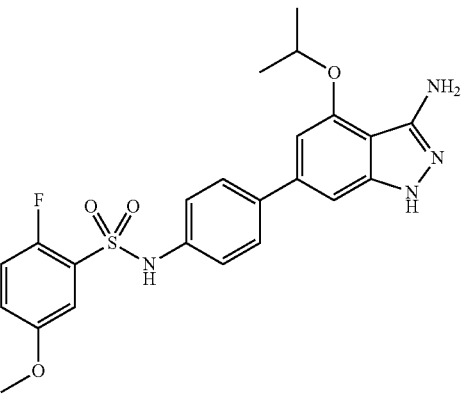 [SMILES: COc1ccc(F)c(S(=O)(=O)Nc2ccc(-c3cc(OC(C)C)c4c(N)n[nH]c4c3)cc2)c1] | 0.064 | 0.1918 | 0.0423 | 0.0588 | | | | |
| 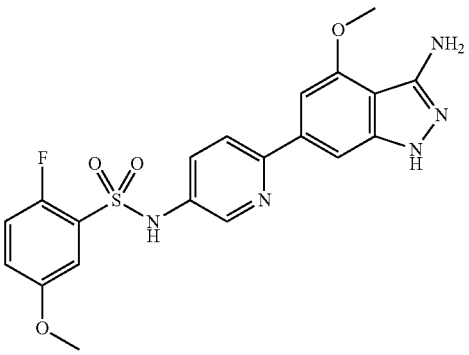 [SMILES: COc1ccc(F)c(S(=O)(=O)Nc2ccc(-c3cc(OC)c4c(N)n[nH]c4c3)nc2)c1] | 0.005 | 0.0065 | 0.013 | 0.0111 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 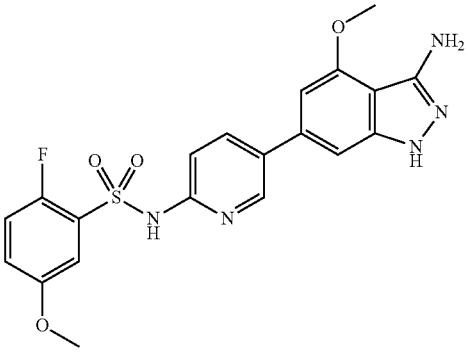 [SMILES: COc1ccc(F)c(S(=O)(=O)Nc2ccc(-c3cc(OC)c4c(N)n[nH]c4c3)cn2)c1] | 0.0072 | 0.0297 | 0.0297 | 0.1331 | | | | |
| 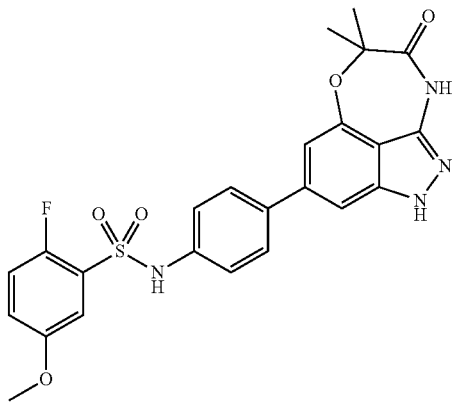 [SMILES: COc1ccc(F)c(S(=O)(=O)Nc2ccc(-c3cc4c5c(n[nH]c5c3)NC(=O)C(C)(C)O4)cc2)c1] | 0.035 | 0.3231 | 0.0776 | 0.3436 | | | | |
| 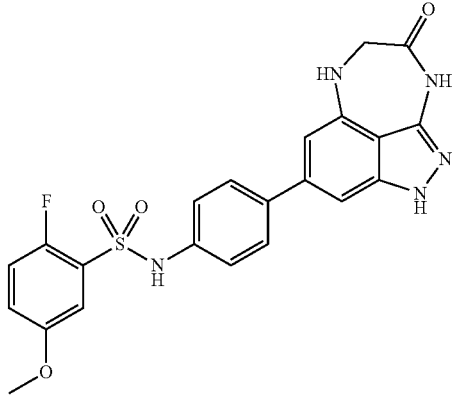 [SMILES: COc1ccc(F)c(S(=O)(=O)Nc2ccc(-c3cc4c5c(n[nH]c5c3)NC(=O)CN4)cc2)c1] | 0.0034 | 0.0186 | 0.0048 | 0.0126 | | | | |

TABLE 2-continued
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 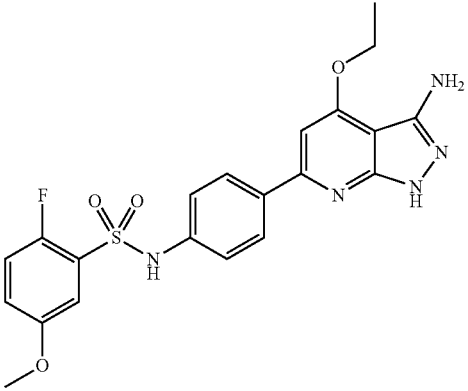 [SMILES: CCOc1cc(-c2ccc(NS(=O)(=O)c3cc(OC)ccc3F)cc2)nc2[nH]nc(N)c12] | 0.0078 | 0.0101 | 0.0162 | 0.0082 | | | | |
| 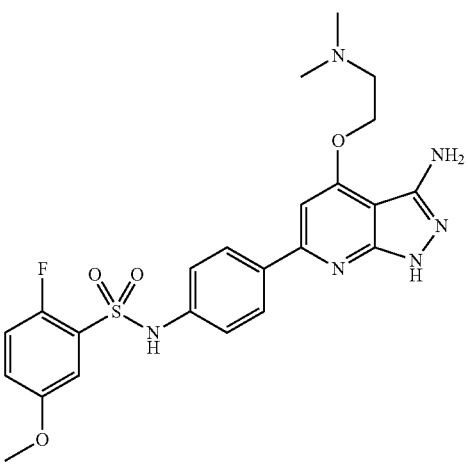 [SMILES: COc1ccc(F)c(S(=O)(=O)Nc2ccc(-c3cc(OCCN(C)C)c4c(N)n[nH]c4n3)cc2)c1] | 0.0042 | 0.04 | 0.045 | 0.1869 | | | | |
| 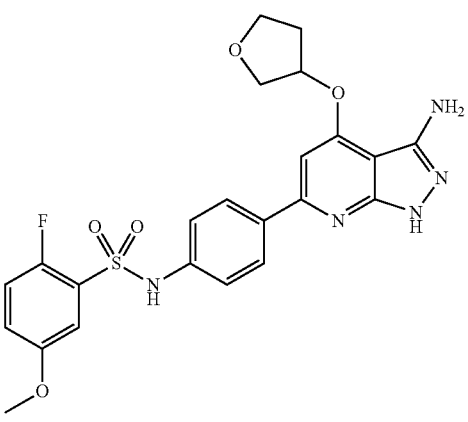 [SMILES: COc1ccc(F)c(S(=O)(=O)Nc2ccc(-c3cc(OC4CCOC4)c4c(N)n[nH]c4n3)cc2)c1] | 0.0076 | 0.0076 | 0.0247 | 0.0089 | | | | |

TABLE 2-continued

Exemplary Testing Results

| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 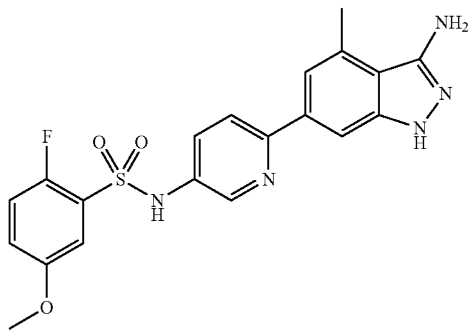 [SMILES: COc1ccc(F)c(S(=O)(=O)Nc2ccc(-c3cc(C)c4c(N)n[nH]c4c3)nc2)c1] | 0.005 | 0.0079 | 0.0101 | 0.0092 | | | | |
| 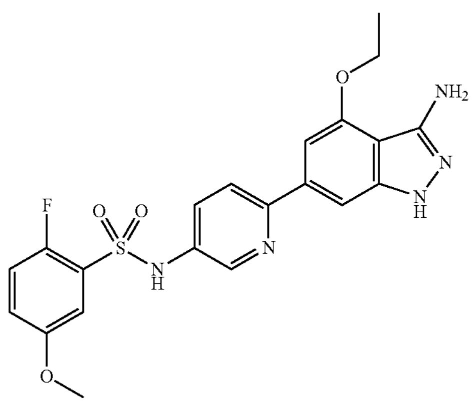 [SMILES: CCOc1cc(-c2ccc(NS(=O)(=O)c3cc(OC)ccc3F)cn2)cc2[nH]nc(N)c12] | 0.075 | 0.0198 | 0.0141 | 0.1096 | | | | |
| 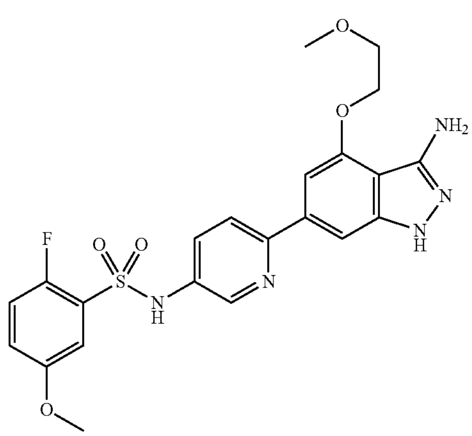 [SMILES: COCCOc1cc(-c2ccc(NS(=O)(=O)c3cc(OC)ccc3F)cn2)cc2[nH]nc(N)c12] | 0.0045 | 0.0332 | 0.04 | 0.0153 | | | | |

TABLE 2-continued

Exemplary Testing Results

| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| (S) isomer structure | 0.0146 | 0.0178 | 0.109 | 0.1812 | | | | |
| (R) isomer structure | 0.004 | 0.036 | 0.0085 | 0.0103 | | | | |
| 5-Cl structure | 0.0059 | 0.169 | 0.0979 | 0.077 | | 2.17 | | |
| 5-OMe structure | 0.0018 | 0.066 | 0.0052 | 0.15 | | >50 | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 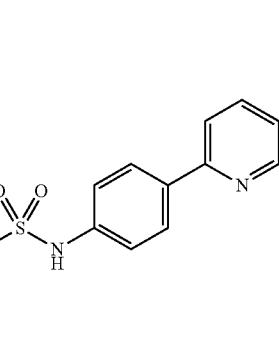 | 0.002 | 0.0065 | 0.0029 | 0.0065 | 0.07 | 21.4 | | |
| 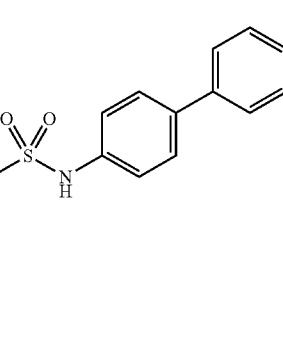 | 0.0218 | 0.5689 | 0.238 | >2.0 | | 20.1 | | |
| 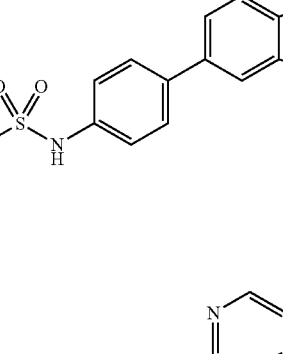 | 0.0321 | 0.664 | 0.124 | 0.352 | | 2.47 | | |
| 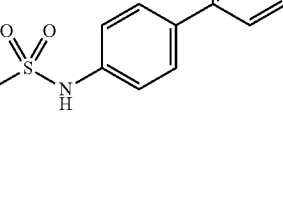 | 0.0067 | 0.068 | 0.0032 | 0.113 | 6.6 | 27.57 | 66.85 | |
| 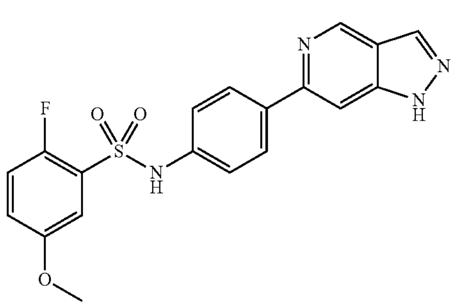 [SMILES: COc1ccc(F)c(S(=O)(=O)Nc2ccc(-c3cc4[nH]ncc4cn3)cc2)c1] | 0.0097 | >0.2 | 0.16 | >0.2 | | | | |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 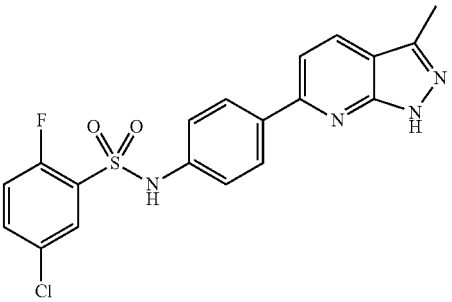 [SMILES: Cc1n[nH]c2nc(-c3ccc(NS(=O)(=O)c4cc(Cl)ccc4F)cc3)ccc12] | 0.0059 | | 0.0121 | | | | | |
| 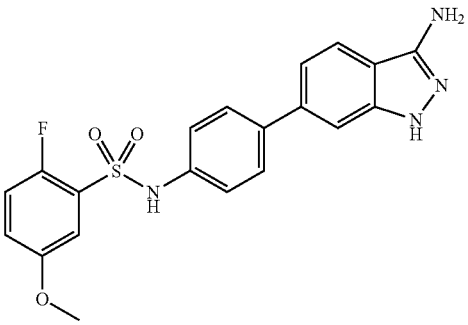 | 0.0061 | 0.016 | 0.0109 | 0.0358 | | 13.7 | 56.12 | 47.1 |
| 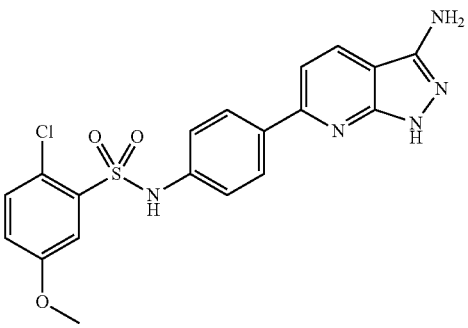 | 0.0021 | 0.0651 | 0.0126 | 0.0677 | | 21.9 | 60.74 | 45.46 |
| 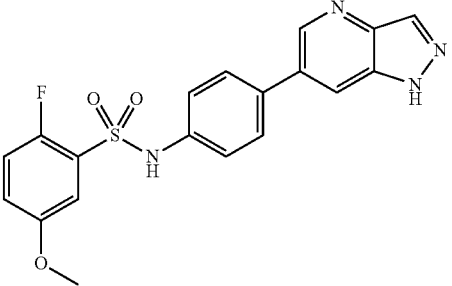 [SMILES: COc1ccc(F)c(S(=O)(=O)Nc2ccc(-c3cnc4cn[nH]c4c3)cc2)c1] | 0.0086 0.0034 | >0.2 | 0.1911 0.0046 | >0.2 | | 13.8 | 66.52 | >100 |

TABLE 2-continued
Exemplary Testing Results
| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| 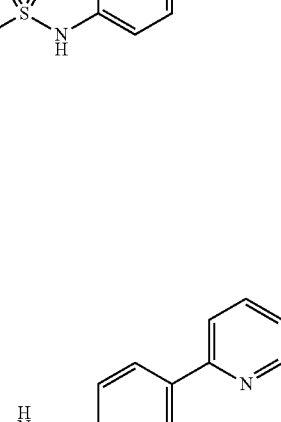 | 0.0055 0.0055 | 0.0541 | 0.0733 0.0023 | >0.2 | | 68.4 | 94.39 | >100 |
| 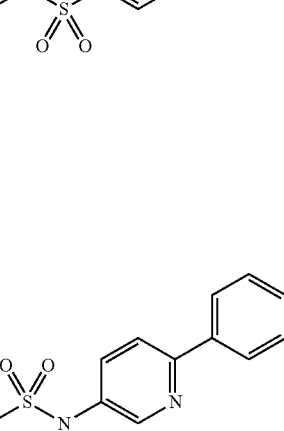 | 0.1088 | | >2.00 | | | | | |
| 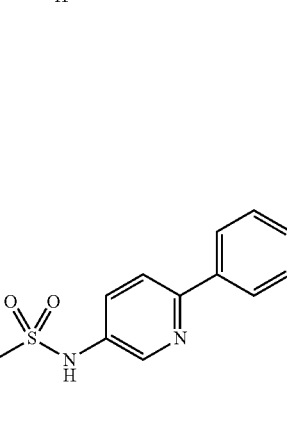 | 0.0046 | 0.0208 | 0.025 | 0.1582 | | | | |
| 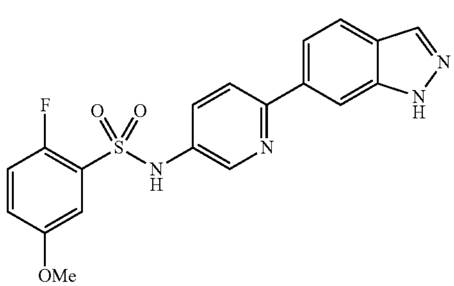 [SMILES: COc1ccc(F)c(S(=O)(=O)Nc2ccc(-c3ccc4cn[nH]c4c3)nc2)c1] | 0.0314 | 0.2671 | 0.0925 | 0.144 | | | | |

TABLE 2-continued

Exemplary Testing Results

| Structure | Sgk2 (50 μM ATP) | Sgk2 (1 mM ATP) | Sgk1 (50 μM ATP) | Sgk1 (1 mM ATP) | Sgk3 | HeLa | 293T | 293T_O |
|---|---|---|---|---|---|---|---|---|
| *structure* | 0.0278 | 0.1341 | 0.1413 | 0.2079 | | | | |
| *structure* | 0.0037 | 0.0075 | 0.0141 | 0.0622 | | | | |
| *structure* | 0.0054 | 0.004 | 0.0179 | 0.0273 | | | | |
| *structure* | 0.0171 | 0.0134 | 0.1504 | 0.5422 | | | | |

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A compound having the structural formula of (I):

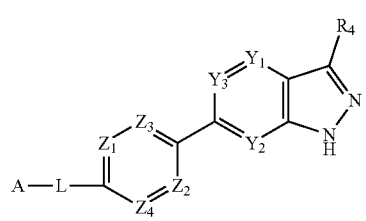

(I)

wherein,
A is

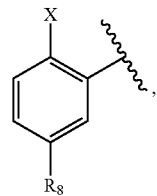

wherein X is a halogen atom and $R_8$ is $OR_9$, wherein $R_9$ is H or a $C_1$-$C_6$ alkyl group;
L is a linking group which is

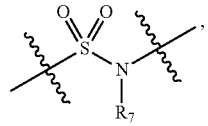

wherein $R_7$ is H;
$Y_1$ is $CR_1$, wherein $R_1$ is a hydrogen, or a $C_1$-$C_6$ alkyl group, —O—$R_h$, —N(R')$R_h$, wherein R' is selected from the group consisting of H and a $C_1$-$C_6$ alkyl group and $R_h$ is a $C_1$-$C_6$ alkyl group;
$Y_2$ is $CR_2$, wherein $R_2$ is H;
$Y_3$ is $CR_3$, wherein $R_3$ is H;
each of $Z_1$ and $Z_4$ is CR, wherein R is H, $Z_3$ is selected from the group consisting of CR and N, wherein R is H or a $C_1$-$C_6$ alkyl group, $Z_2$ is N; and
$R_4$ is H, a $C_1$-$C_6$ alkyl group, —N(R')R", —N(R')—C(O)R", —N(R')—C(O)—NH—R", wherein each of R' and R" is independently selected from the group consisting of H and a $C_1$-$C_6$ alkyl group,
or a pharmaceutically acceptable salt, hydrate, solvate, stereoisomer.

2. The compound of claim 1, wherein $Z_3$ is CR, wherein R is H.

3. The compound of claim 1, wherein X is F or Cl, $R_4$ is $NH_2$, $R_8$ is $OR_9$, wherein $R_9$ is a hydrogen.

4. The compound of claim 1, wherein X is F, $R_9$ is $CH_3$.

5. A compound is:
N-(6-(3-amino-4-methyl-1H-indazol-6-yl)pyridin-3-yl)-2-fluoro-5-methoxybenzenesulfonamide;
N-(6-(3-amino-4-ethoxy-1H-indazol-6-yl)pyridin-3-yl)-2-fluoro-5-methoxybenzenesulfonamide;
N-(6-(3-amino-4-(2-methoxyethoxy)-1H-indazol-6-yl)pyridin-3-yl)-2-fluoro-5-methoxybenzenesulfonamide;
(S)—N-(6-(3-amino-4-((tetrahydrofuran-3-yl)oxy)-1H-indazol-6-yl)pyridin-3-yl)-2-fluoro-5-methoxybenzenesulfonamide;
(R)—N-(6-(3-amino-4-((tetrahydrofuran-3-yl)oxy)-1H-indazol-6-yl)pyridin-3-yl)-2-fluoro-5-methoxybenzenesulfonamide;
N-(6-(3-amino-1H-indazol-6-yl)pyridin-3-yl)-2-fluoro-5-methoxybenzenesulfonamide;
N-(6-(1H-indazol-6-yl)pyridin-3-yl)-2-fluoro-5-methoxybenzenesulfonamide;
N-(2-(3-amino-1H-indazol-6-yl)pyrimidin-5-yl)-2-fluoro-5-methoxybenzenesulfonamide;
N-(2-(3-amino-4-methoxy-1H-indazol-6-yl)pyrimidin-5-yl)-2-fluoro-5-methoxybenzenesulfonamide, and
N-(6-(3-amino-4-methoxy-1H-indazol-6-yl)pyridin-3-yl)-2-fluoro-5-methoxybenzenesulfonamide.

6. A pharmaceutical composition, comprising a compound of claim 1, or a pharmaceutically acceptable salt, hydrate, solvate, stereoisomer; and a pharmaceutically acceptable excipient, carrier, or diluent.

\* \* \* \* \*